(12) United States Patent
Moriya et al.

(10) Patent No.: US 8,257,955 B2
(45) Date of Patent: Sep. 4, 2012

(54) ENDOGLUCANASE PPCE AND CELLULASE PREPARATION CONTAINING THE SAME

(75) Inventors: Tatsuki Moriya, Odawara (JP); Akitaka Nakane, Chuo-ku (JP); Goh Tsujiuchi, Odawara (JP); Takayoshi Fukushima, Odawara (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 268 days.

(21) Appl. No.: 12/531,041

(22) PCT Filed: Mar. 12, 2008

(86) PCT No.: PCT/JP2008/054511
§ 371 (c)(1),
(2), (4) Date: Sep. 11, 2009

(87) PCT Pub. No.: WO2008/111613
PCT Pub. Date: Sep. 18, 2008

(65) Prior Publication Data
US 2010/0098807 A1 Apr. 22, 2010

(30) Foreign Application Priority Data

Mar. 12, 2007 (JP) .................................. 2007-061266

(51) Int. Cl.
C12N 9/42 (2006.01)
C12N 1/00 (2006.01)
C12N 15/00 (2006.01)
C12P 7/06 (2006.01)
D06M 16/00 (2006.01)
D06M 13/00 (2006.01)
A23C 9/12 (2006.01)
C11D 3/00 (2006.01)
C07H 21/04 (2006.01)
C07K 1/00 (2006.01)

(52) U.S. Cl. .................. 435/209; 435/161; 435/254.1; 435/254.2; 435/254.3; 435/254.5; 435/254.6; 435/320.1; 435/263; 426/63; 510/320; 530/350; 536/23.1; 536/23.2; 8/102

(58) Field of Classification Search .................. 435/209, 435/161, 254.11, 254.2, 254.3, 254.5, 254.6; 435/320.1, 263; 426/63; 510/320; 530/350; 536/23.1, 23.2; 8/102
See application file for complete search history.

(56) References Cited

U.S. PATENT DOCUMENTS

| | | | |
|---|---|---|---|
| 6,159,720 A | 12/2000 | Murashima et al. | |
| 6,403,362 B1 | 6/2002 | Moriya et al. | |
| 6,921,655 B1 | 7/2005 | Nakamura et al. | |
| 7,273,748 B2 * | 9/2007 | Miettinen-Oinonen et al. | 435/263 |
| 2005/0143275 A1 | 6/2005 | Murashima et al. | |
| 2007/0111278 A1 | 5/2007 | Koga et al. | |

FOREIGN PATENT DOCUMENTS

| | | |
|---|---|---|
| EP | 0 307 564 A2 | 3/1989 |
| JP | 2004-313022 A | 11/2004 |
| RU | 2 238 974 C2 | 7/2003 |
| WO | 91/17243 A1 | 11/1991 |
| WO | 98/03640 A1 | 1/1998 |
| WO | 98/03667 A1 | 1/1998 |
| WO | 98/54332 A1 | 12/1998 |
| WO | WO 00/14208 A1 | 3/2000 |
| WO | 00/24879 A1 | 5/2000 |
| WO | 01/90375 A1 | 11/2001 |
| WO | 2005/054475 A1 | 6/2005 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
K. Mahalingeshwara Bhat, et al., "The Endo-(1→4)-β-D-Glucanase System of *Penicillium pinophilum*Cellulase: Isolation, Purification, and Characterization of Five Major Endoglucanase Components," Carbohydrate Research, (1989), pp. 279-297, vol. 190.
Hirofumi Okada, et al., "Molecular Characterization and Heterologous Expression of the Gene Encoding a Low-Molecular-Mass Endoglucanase from *Trichoderma reesei* QM9414," Applied and Environmental Microbiology, Feb. 1998, pp. 555-563, vol. 64, No. 2.
Toshihiko Ooi, et al., "Complete nucleotide sequence of a gene coding for *Aspergillus aculeatus* cellulase (Fl-CMCase)," Nucleic Acids Research, (1990), p. 5884, vol. 18, No. 19.
Goedegebuur Frits et al: "Cloning and relational analysis of 15 novel fungal endoglucanases from family 12 glycosyl hydrolase" Current Genetics, New York, NY, US, vol. 41, No. 2, May 1, 2002, pp. 89-98, XP002436805 ISSN: 0172-8083.

* cited by examiner

*Primary Examiner* — Ganapathirama Raghu
(74) *Attorney, Agent, or Firm* — Sughrue Mion, PLLC

(57) ABSTRACT

A novel endoglucanase PPCE derived from *Penicillium pinophilum*, a cellulase preparation containing the endoglucanase PPCE, and a method of treating a cellulose-containing fabric utilizing the endoglucanase PPCE or the cellulase preparation, are disclosed. The endoglucanase PPCE is highly active to a fabric, and has a low optimum temperature and a strongly acidic optimum pH.

24 Claims, No Drawings

ENDOGLUCANASE PPCE AND CELLULASE PREPARATION CONTAINING THE SAME

TECHNICAL FIELD

The present invention relates to an endoglucanase PPCE, a cellulase preparation containing the endoglucanase PPCE, and a method of treating a cellulose-containing fabric utilizing the endoglucanase PPCE or the cellulase preparation.

BACKGROUND ART

Conventionally, a cellulose-containing fabric has been treated with cellulase to impart desired properties to the fabric. For example, in the textile industry, a treatment with cellulase is carried out to improve the touch feel and appearance of a cellulose-containing fabric, or to impart a "stonewash" appearance to a colored cellulose-containing fabric, thereby providing the fabric with localized color change [patent reference 1].

Cellulases used for such uses include endoglucanases belonging to family 45, endoglucanases belonging to family 5, and endoglucanases belonging to family 12. It is normal in this technical field that these endoglucanases may be appropriately selected in accordance with their properties (for example, an optimum pH, an optimum temperature, an effect to improve the texture of a fabric, or an influence on fiber strength). Endoglucanases belonging to family 45 are mainly used under neutral conditions, endoglucanases belonging to family 12 are used under acidic conditions to neutral conditions, and endoglucanases belonging to family 5 are mainly used under acidic conditions. Examples of endoglucanases belonging to family 45 include a purified 43 kDa endoglucanase component derived from genus *Humicola* [patent reference 2], endoglucanase NCE5 derived from genus *Humicola* [patent reference 3], and endoglucanase RCE I derived from genus *Rhizopus* [patent reference 4].

Examples of endoglucanases belonging to family 5 include endoglucanase SCE3 derived from genus *Trichoderma* [patent reference 5]. Examples of endoglucanases belonging to family 12 include endoglucanase EG III derived from genus *Trichoderma* [non-patent reference 1] and endoglucanase FI-CMCase derived from genus *Aspergillus* [non-patent reference 2]. It is known that genus *Penicillium* produces endoglucanase having a molecular weight of 25 kDa [non-patent reference 3].

When these enzymes are used for fabric processing, reactions are generally carried out under optimum conditions. Optimum temperatures of these known enzymes are within a middle temperature area (for example, 40° C. to 60° C.), and optimum pHs thereof are around between an acidic condition and a neutral condition (for example, pH 4.0 to pH 8.0). In this technical field, there is no case of an enzyme having a low optimum temperature (such as lower than 40° C.) or a strongly acidic optimum pH (such as less than pH 4.0) being commonly used industrially. In industrial processing of cellulose-containing fabrics, a cellulase preparation is commonly provided as a preparation comprising a large amount of endoglucanase having a high activity. As a process for manufacturing such a preparation, processes of overexpressing a desired endoglucanase component having a high activity in host cells using genetic recombinant techniques are known [patent references 6, 7].

As preferable host cells used in these processes, there may be mentioned, for example, filamentous fungi belonging to Hyphomycetes, such as filamentous fungi belonging to genus *Aspergillus*, *Humicola*, or *Trichoderma*. When cellulase used in fabric processing under acidic or strongly acidic condition is produced, genus *Trichoderma* producing acidic cellulase is preferable as host cells, by comparison with genus *Aspergillus* or *Humicola* producing neutral cellulase, because a synergistic effect caused by cellulase derived from the host is expected. Particularly, in view of the industrial production of the enzyme, the filamentous fungi belonging to genus *Trichoderma* having a high productivity is most preferable [patent reference 8]. However, when a filamentous fungus belonging to genus *Trichoderma* is used to express a gene derived from a different species (i.e., exogenous gene), the expression is often inhibited because features in the nucleotide sequence of the gene (such as codon usage in the gene) are different. In this case, it is necessary to modify the exogenous gene. For example, when endoglucanase RCE I derived from genus *Rhizopus* belonging to Zygomycetes is overexpressed in *Humicola insolens*, the gene encoding RCE I should be optimized in accordance with the codon usage of the host cell [patent reference 4]. However, if such an optimization is carried out, it will be difficult to express an exogenous gene as much as endogenous genes. Further, even when the enzyme of interest is actually expressed and produced in a host, it is anticipated that the enzyme is digested with proteases or the like contained in a culture liquid during cultivation to obtain the enzyme as digested products or partial fragments.

[patent reference 1] European Patent No. 307,564
[patent reference 2] International Publication WO98/03640
[patent reference 3] International Publication WO01/090375
[patent reference 4] International Publication WO00/24879
[patent reference 5] International Publication WO98/54332
[patent reference 6] International Publication WO91/17243
[patent reference 7] International Publication WO98/03667
[patent reference 8] International Publication WO05/054475
[non-patent reference 1] Okada, H. et. al., "Appl. Environ. Microbiol", 64, 1998, p. 555-563
[non-patent reference 2] Ooi, T. et. al., "Nucleic Acids Research", 18, 1990, p. 5884
[non-patent reference 3] K. Mahalingeshwara et. al., "Carbohydrate Research" 190, 1989, p. 279-297

DISCLOSURE OF THE INVENTION

Problems to be Solved by the Invention

For use in fabric processing, various cellulases were isolated from filamentous fungi belonging to genus *Humicola, Trichoderma, Rhizopus, Mucor, Phycomyces, Staphylotrichum* or the like, and genes encoding the cellulases were also isolated. In particular, enzyme groups belonging to cellulase family 5, family 12, and family 45, derived from filamentous fungi, exhibit advantageous activities in fabric processing, and thus, are widely used in this technical field. However, these enzyme groups are enzymes having a moderate optimum temperature and an acidic or neutral optimum pH, but there is not a low-temperature enzyme nor a strongly acidic enzyme. In this technical field, an enzyme having a high activity against fibers and a low optimum temperature and/or a strongly acidic optimum pH is strongly desired. Further, to practically use an enzyme having such specific profile, it is necessary to attain the overexpression of a gene of interest in an excellent host, such as filamentous fungi belonging to genus *Trichoderma*, and to provide a cellulase preparation having a high activity at a small cost. If such a cellulase preparation is practically provided, it will bring enormous industrial benefits. However, such a cellulase preparation has not been practically provided, and such a process using genetic recombinant techniques is not reported.

Means for Solving the Problems

The present inventors found a novel protein having endoglucanase activity and a gene thereof from *Penicillium pinophilum* PF1365 (FERM BP-10780). The present invention provides endoglucanase PPCE, a cellulase preparation containing endoglucanase PPCE, and a method of treating a cellulose-containing fabric utilizing endoglucanase PPCE or the cellulase preparation. The present inventors found that the novel protein having endoglucanase activity, which was isolated from *Penicillium pinophilum* PF1365 (FERM BP-10780), exhibited extremely high activities to improve the appearance of a cellulose-containing fabric and to impart a "stonewash" appearance to a colored cellulose-containing fabric. In particular, endoglucanase PPCE (hereinafter, simply referred to "PPCE") exhibited a remarkably high activity in fabric processing, by comparison with endoglucanase SCE3 [patent reference 5] and endoglucanase EG III [non-patent reference 1], which are widely used as a typical cellulase for fabric processing, mainly under acidic conditions. Further, endoglucanase PPCE exhibited surprising features that its optimum pH and optimum temperature were remarkably low, i.e., around pH 3 and 30° C., respectively, by comparison with known cellulases for fabric processing. Even if compared with the optimum temperature (50 to 55° C.) and the optimum pH (pH 4.0 to 5.0) of endoglucanase I derived from *Penicillium pinophilum* IMI87160ii [non-patent reference 3], which had not been used in fabric processing, the optimum pH and optimum temperature of endoglucanase PPCE were remarkably low.

The present inventors isolated a gene encoding endoglucanase PPCE derived from *Penicillium pinophilum* PF1365 (FERM BP-10780), and attained an industrially large-scale production of PPCE in *Trichoderma viride* utilizing a regulatory sequence of a cellulase cbhI gene (WO98/11239). Therefore, the present invention provides the novel protein having endoglucanase activity derived from *Penicillium pinophilum* PF1365 (FERM BP-10780) and the gene thereof, and a cellulase preparation containing the protein and having excellent properties. Further, the present invention provides a host cell transformed with the gene encoding the protein, and a method of obtaining the protein of interest by cultivating the host cell. Furthermore, the present invention provides a method of treating a cellulose-containing fabric with the protein of the present invention or the cellulase preparation of the present invention.

Therefore, the present invention includes the following inventions.

(1) A protein having the following properties (a), (b), and (c):
(a) derived from *Penicillium pinophilum*,
(b) having an endoglucanase activity, and
(c) having at the N-terminus thereof (1) the amino acid sequence of SEQ ID NO: 2, or (2) an amino acid sequence in which one amino acid is deleted, substituted, or added in the amino acid sequence of SEQ ID NO: 2.

(2) The protein of (1), having the following property (d):
(d) having an average molecular weight of 25 kDa to 27 kDa, determined by a sodium dodecyl sulfate-polyacrylamide gel electrophoresis (SDS-PAGE).

(3) A protein selected from the group consisting of the following proteins (e) to (i):
(e) a protein comprising the amino acid sequence consisting of amino acids 16-236 of SEQ ID NO: 4,
(f) a protein comprising the amino acid sequence consisting of amino acids 1-236 of SEQ ID NO: 4,
(g) a protein comprising the amino acid sequence of SEQ ID NO: 30,
(h) a modified protein comprising an amino acid sequence in which one or plural amino acids are deleted, substituted, added and/or modified in the amino acid sequence consisting of amino acids 16-236 or 1-236 of SEQ ID NO: 4, and having an endoglucanase activity, and
(i) a homologous protein comprising an amino acid sequence having a 90% homology or more with the amino acid sequence consisting of amino acids 16-236 or 1-236 of SEQ ID NO: 4 or with the amino acid sequence of SEQ ID NO: 30, and having an endoglucanase activity.

(4) A polynucleotide encoding the protein of any one of (1) to (3).

(5) A polynucleotide selected from the following (j) or (k):
(j) a polynucleotide comprising the nucleotide sequence of SEQ ID NO: 3 or 28, or the nucleotide sequence consisting of nucleotides 46-834 of SEQ ID NO: 3 or 28, or
(k) a polynucleotide comprising a nucleotide sequence in which one or plural nucleotides are deleted, substituted, and/or added in the nucleotide sequence of SEQ ID NO: 3 or 28 or the nucleotide sequence consisting of nucleotides 46-834 of SEQ ID NO: 3 or 28, and encoding a protein having an endoglucanase activity.

(6) An expression vector comprising the polynucleotide of (4) or (5).

(7) A host cell transformed with the expression vector of (6).

(8) The host cell of (7), wherein the host is a yeast or a filamentous fungus.

(9) The host cell of (8), wherein the filamentous fungus is a microorganism belonging to genus *Trichoderma, Humicola, Aspergillus, Acremonium*, or *Penicillium*.

(10) The host cell of (9), wherein the filamentous fungus is a microorganism belonging to genus *Trichoderma*.

(11) The host cell of (10), wherein the filamentous fungus is *Trichoderma viride*.

(12) A process for producing the protein of any one of (1) to (3), comprising the steps of: cultivating the host cells of any one of (7) to (11), and collecting the protein from the host cells or a culture obtained by the cultivation.

(13) A protein produced by the process of (12).

(14) A cellulase preparation comprising the protein of any one of (1) to (3) and (13).

(15) A detergent composition comprising the protein of any one of (1) to (3) and (13) or the cellulase preparation of (14).

(16) A method of treating a cellulose-containing fabric, comprising the step of bringing the cellulose-containing fabric into contact with the protein of any one of (1) to (3) and (13), the cellulase preparation of (14), or the detergent composition of (15).

(17) A method of reducing weight to improve the touch feel and appearance of a cellulose-containing fabric, comprising the step of bringing the cellulose-containing fabric into contact with the protein of any one of (1) to (3) and (13), the cellulase preparation of (14), or the detergent composition of (15).

(18) A method of providing a localized color change to a colored cellulose-containing fabric, comprising the step of bringing the colored cellulose-containing fabric into contact with the protein of any one of (1) to (3) and (13), the cellulase preparation of (14), or the detergent composition of (15).

(19) A method of color clarification of a colored cellulose-containing fabric, comprising the step of bringing the colored cellulose-containing fabric into contact with the protein of any one of (1) to (3) and (13), the cellulase preparation of (14), or the detergent composition of (15).

(20) A method of reducing fuzzing of a cellulose-containing fabric or reducing a rate of the formation of fuzz, comprising the step of bringing the cellulose-containing fabric into contact with the protein of any one of (1) to (3) and (13), the cellulase preparation of (14), or the detergent composition of (15).

(21) A method of reducing stiffness of a cellulose-containing fabric or reducing a rate of the formation of stiffness, comprising the step of bringing the cellulose-containing fabric into contact with the protein of any one of (1) to (3) and (13), the cellulase preparation of (14), or the detergent composition of (15).

(22) The method of any one of (16) to (21), wherein the contacting step of the fabric with the detergent composition is carried out by soaking, washing, or rinsing the fabric.

(23) A method of deinking waste paper, characterized by using the protein of (1) to (3) and (13) or the cellulase preparation of (14), in the process of treating the waste paper together with a deinking agent.

(24) A method of improving a water freeness of paper pulp, comprising the step of treating the paper pulp with the protein of any one of (1) to (3) and (13), or the cellulase preparation of (14).

(25) A method of improving a digestibility of animal feed, comprising the step of treating an animal feed with the protein of any one of (1) to (3) and (13), or the cellulase preparation of (14).

(26) A method of producing biomass ethanol by digesting and saccharifying a cellulose-based substance, comprising the step of treating the cellulose-based substance with the protein of any one of (1) to (3) and (13), or the cellulase preparation of (14).

Effects of the Invention

The protein of the present invention, endoglucanase PPCE, is available for washing or fabric processing, such as improvement of the touch feel and appearance of a cellulose-containing fabric, providing a localized color change to the fabric, color clarification, reduction of fuzz or a reduction of stiffness.

BEST MODE FOR CARRYING OUT THE INVENTION

Protein having Endoglucanase Activity

The term "endoglucanase" as used herein means an enzyme exhibiting an endoglucanase activity, i.e., endo-1,4-β-glucanase (EC 3.2.1.4), which has an activity of hydrolyzing the β-1,4-glucopyranosyl bond of β-1,4-glucan.

The term "endoglucanase activity" as used herein means a CMCase activity. The term "CMCase activity" as used herein means an activity of hydrolyzing carboxymethylcellulose (CMC; Tokyo Kasei Kogyo Co., Ltd.). When a solution containing a protein (enzyme) to be assayed and CMC is incubated for a predetermined period and the amount of reducing sugar released is measured, the amount of the enzyme producing the reducing sugar corresponding to 1 μmol of glucose per minute is defined as 1 unit of CMCase activity.

The endoglucanase activity can be measured, for example, by the following procedure. That is, 0.5 mL of a solution containing a protein to be assayed is added to 0.5 mL of a 2% CMC solution dissolved in a 50 mmol/L acetate-sodium acetate buffer (pH6.0), and the mixture is incubated at 50° C. for 30 minutes. A concentration of reducing sugar generated in the reaction mixture is measured by the 3,5-dinitrosalicylic acid method (DNS method). More particularly, after incubation for 30 minutes, 3.0 mL of a DNS reagent is added to 1.0 mL of the reaction mixture, the whole is incubated in a boiling water bath for 5 minutes and diluted with 8.0 mL of distilled water, and the absorbance at 540 nm is measured. A calibration curve is produced using glucose solutions prepared by stepwise dilution, and an amount of reducing sugar generated in the enzyme reaction mixture is determined as that of converted glucose. The activity is calculated by defining as 1 unit the amount of the enzyme producing the reducing sugar corresponding to 1 μmol of glucose per minute.

The DNS reagent can be prepared in accordance with disclosures in references such as Sakuzo Hukui, "Seikagaku Jikken-hou 1, Kangen-Tou no Teiryo-hou (Laboratory Manual for Biological Chemistry, Vol. 1, Assay of Reducing Sugar)", pp. 19-20, Japan Scientific Societies Press, or by the following procedure. To 300 mL of a 4.5% aqueous solution of sodium hydrate, 880 mL of a 1% 3,5-dinitrosalicylic acid solution and 255 g of Rochelle salt are added (Solution A). To 22 mL of a 1.0% aqueous solution of sodium hydrate, 10 g of crystalline phenol is added, and then water is added to dissolve it and adjust the volume to 100 mL (Solution B). Then, 6.9 g of sodium hydrogencarbonate is dissolved in 69 mL of Solution B, and Solution A is poured thereinto. The whole is mixed with stirring to dissolve the Rochelle salt, allowed to stand for 2 days, and then filtrated.

The protein of the present invention may be obtained from filamentous fungi, such as a microorganism belonging to genus *Penicillium*, preferably *Penicillium pinophilum*, more preferably *Penicillium pinophilum* PF1365 (FERM BP-10780), and a mutant strain derived therefrom may be used. The N-terminal amino acid sequence of the protein of the present invention is typically that of SEQ ID NO: 2. The N-terminal amino acid sequence may be determined, for example, in accordance with the procedure described in Example 2. According to the present invention, a protein derived from *Penicillium pinophilum*, and having the following properties (A), (B), and (C):

(A) having endoglucanase activity, (B) having at the N-terminus thereof (1) the amino acid sequence of SEQ ID NO: 2, or (2) an amino acid sequence in which one amino acid is deleted, substituted, or added in the amino acid sequence of SEQ ID NO: 2, and (C) having an average molecular weight of 25 kDa to 27 kDa, determined by SDS-PAGE, is provided.

The average molecular weight determined by SDS-PAGE may be determined in accordance with the procedure described in Example 1.

The protein of the present invention derived from *Penicillium pinophilum* typically consists of the amino acid sequence consisting of amino acids 16-236 of SEQ ID NO: 4, and the N-terminal glutamine (Gln) residue is converted to a pyroglutamic acid (pyroGlu) residue by modification (that is, the protein consists of the amino acid sequence of SEQ ID NO: 30).

According to another embodiment of the present invention, a protein comprising the amino acid sequence of SEQ ID NO: 4 (or a partial sequence thereof), and a modified protein or a homologous protein thereof, are provided.

Examples of "the protein comprising the amino acid sequence of SEQ ID NO: 4 or a partial sequence thereof" include:
a mature protein having the amino acid sequence consisting of amino acids 16-236 of SEQ ID NO: 4;

a precursor protein comprising the amino acid sequence consisting of amino acids 1-236 of SEQ ID NO: 4 in which a signal peptide (1st to 15th positions) is added;

a protein consisting of an amino acid sequence in which one or more appropriate sequences are added to the N-terminus and/or the C-terminus of the mature protein having the amino acid sequence consisting of amino acids 16-236 of SEQ ID NO: 4; and a protein in which the N-terminal amino acid and/or the C-terminal amino acid of the mature protein having the amino acid sequence consisting of amino acids 16-236 of SEQ ID NO: 4 are modified.

The term "addition of amino acid sequence" as used herein includes an addition of part or the whole of the signal peptide consisting of amino acids 1-15 of SEQ ID NO: 4 to the N-terminus of the mature protein having the amino acid sequence consisting of amino acids 16-236 of SEQ ID NO: 4.

The term "modification of amino acid sequence" as used herein includes a modification of the N-terminus of the mature protein having the amino acid sequence consisting of amino acids 16-236 of SEQ ID NO: 4 by an enzyme derived from a host. This modification includes a modification of the N-terminal glutamine (Gln) residue of the mature protein to a pyroglutamic acid (pyroGlu) residue.

Examples of the signal peptide include the amino acid sequence consisting of amino acids 1-15 of SEQ ID NO: 4, that is, the amino acid sequence consisting of 15 amino acid residues encoded by the nucleotide sequence from the ATG codon at the 1st to 3rd positions to the codon at the 43rd to 45th positions.

The term "modified protein" as used herein means a protein comprising an amino acid sequence in which one or plural amino acids (preferably one or several amino acids) are deleted, substituted, added, and/or modified in the amino acid sequence of SEQ ID NO: 4 (or a partial sequence thereof), and having endoglucanase activity.

The number of amino acids to be modified such as "deleted, substituted, or added" is one or plural amino acids (preferably one or several amino acids), for example, 1 to 20, preferably 1 to 10, more preferably 1 to 5, most preferably 1 to 3. The modified protein includes a protein comprising an amino acid sequence in which one or plural amino acids are conservatively substituted in the amino acid sequence of SEQ ID NO: 4, and having endoglucanase activity.

The term "conservative substitution" as used herein means that one or plural amino acid residues contained in a protein are replaced with different amino acids having similar chemical properties so that the activities of the protein are not substantially changed. As the conservative substitution, there may be mentioned, for example, a substitution of a hydrophobic residue for another hydrophobic residue, or a substitution of a polar residue for another polar residue with the same charge. Amino acids which have similar chemical properties and can be conservatively substituted for each other are known to those skilled in the art.

More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine.

As acidic amino acids having a negative charge, there may be mentioned, for example, aspartic acid or glutamic acid.

The protein of the present invention may be isolated and purified from a microorganism, for example, as described in Example 1. The protein of the present invention may be obtained by expressing a polynucleotide encoding the protein of the present invention in an appropriate host by genetic recombinant techniques, and isolating and purifying the produced protein, as described below.

Examples of the homologous protein of the present invention include a protein comprising an amino acid sequence having a 90% homology or more (preferably 95% or more, more preferably 98% or more, most preferably 99% or more) with the amino acid sequence consisting of amino acids 16-236 or 1-236 of SEQ ID NO: 4 or with the amino acid sequence of SEQ ID NO: 30, and having endoglucanase activity. The homology as used herein is shown as a value calculated by a commercially available Genetic Information Processing Software GENETYX (GENETYX Corporation), in accordance with default parameters in a homology search program.

Default Parameters:
Unit Size to Compare=2
Pick up Location=1
Polynucleotide Encoding Protein having Endoglucanase Activity According to the present invention, polynucleotides encoding a protein comprising the amino acid sequence of SEQ ID NO: 4 or a partial sequence thereof, or a modified protein thereof are provided. When the amino acid sequence of a protein is given, a nucleotide sequence encoding the amino acid sequence can be easily selected, and thus various nucleotide sequences encoding the protein of the present invention can be selected. The term "polynucleotide" as used herein includes DNA and RNA, and DNA is preferable.

Typically, the polynucleotide of the present invention may be selected from the group consisting of:

(a) a polynucleotide comprising the nucleotide sequence of SEQ ID NO: 3 or 28 (or a partial sequence thereof), and (b) a polynucleotide comprising a nucleotide sequence in which one or plural nucleotides are deleted, substituted, and/or added in the nucleotide sequence of SEQ ID NO: 3 or 28 (or a partial sequence thereof), and encoding a protein having endoglucanase activity.

Examples of the polynucleotide comprising the nucleotide sequence of SEQ ID NO: 3 or a partial sequence thereof include a polynucleotide having the nucleotide sequence consisting of nucleotides 1-834 of SEQ ID NO: 3, and a polynucleotide having the nucleotide sequence consisting of nucleotides 46-834 of SEQ ID NO: 3.

The polynucleotide of the present invention includes a naturally-occurring polynucleotide. Further, the whole can be synthesized. Furthermore, the synthesis may be carried out using part of the naturally-occurring polynucleotide. Typically, the polynucleotide of the present invention may be obtained by performing a PCR reaction using genomic DNA of *Penicillium pinophilum* as a template. Further, the polynucleotide of the present invention may be obtained in accordance with an ordinary method commonly used in genetic engineering, for example, by preparing a genomic DNA library and screening the library using an appropriate DNA probe designed on the basis of information of a partial amino acid sequence.

In the present invention, a typical nucleotide sequence encoding the amino acid sequence of endoglucanase PPCE has the nucleotide sequence of SEQ ID NO: 3. The nucleotide sequence of SEQ ID NO: 3 has an open reading frame from the ATG codon at the 1st to 3rd positions to the TAG codon at the 832nd to 834th positions and two introns at the 411th to 469th and 691st to 754th positions. The nucleotide sequence at the 46th to 48th positions corresponds to the N-terminal amino acid of a mature protein of endoglucanase PPCE consisting of 221 amino acid residues.

Expression Vector and Transformant

According to the present invention, an expression vector comprising a polynucleotide encoding a protein comprising the amino acid sequence of SEQ ID NO: 4 or a partial sequence thereof, or a modified protein (hereinafter referred to as the polynucleotide of the present invention) so that the polynucleotide may be replicated and the protein encoded by the polynucleotide may be expressed in a host microorganism, is provided. The expression vector of the present invention can be constructed on the basis of a self-replicating vector (such as a plasmid), which exists as an extrachromosomal element and can replicate independently of the replication of chromosomes. Alternatively, the expression vector of the present invention may be a vector which is integrated into the genome of the host microorganism and replicated together with chromosomes, when the host is transformed with the vector. The construction of the vector of the present invention can be carried out by ordinary procedures or methods commonly used in genetic engineering. To express a protein having a desired activity by transforming a host microorganism with the expression vector of the present invention, it is preferable that the expression vector contains, for example, a polynucleotide capable of controlling the expression, in addition to the polynucleotide of the present invention. As the polynucleotide capable of controlling the expression, for example, a promoter, a terminator, or a polynucleotide encoding a signal peptide, may be used in the present invention. The promoter which can be used in the present invention is not particularly limited, so long as it shows a transcriptional activity in a host microorganism. The promoter can be obtained as a polynucleotide which controls the expression of a gene encoding a protein the same as or different from that derived from the host microorganism.

The signal peptide is not particularly limited, so long as it contributes to the protein secretion in a host microorganism. The signal peptide can be obtained as a polynucleotide derived from a gene encoding a protein the same as or different from that derived from the host microorganism.

The expression vector of the present invention may contain a genetic marker to select a transformant obtained by introducing the expression vector into a host microorganism. The genetic marker can be appropriately selected in accordance with the method for selecting a transformant. As the genetic marker, for example, a drug resistance gene or a gene complementing an auxotrophic mutation can be used in the present invention.

The genetic marker may be inserted into a vector other than the expression vector, and this vector containing the genetic marker may be mixed with the expression vector to transform a host with these vectors simultaneously (also called cotransform). According to the present invention, a microorganism transformed with the expression vector is provided. A host-vector system which can be used in the present invention is not particularly limited. For example, a system utilizing *E. coli*, *Actinomycetes*, yeasts, or filamentous fungi, or a system for the expression of a fusion protein using such a microorganism can be used. Transformation of a microorganism with the expression vector can be carried out in accordance with an ordinary method. In the present invention, the transformant of the present invention is cultured, and the resulting transformant or culture is used to obtain the protein of the present invention. According to another embodiment of the present invention, the process for producing the novel protein of the present invention can be provided. Cultivation of the transformant (including culturing conditions) can be carried out in a fashion substantially similar to that of the original host used to prepare the transformant.

As the method for recovering the protein of interest after the cultivation of the transformant, commonly used procedures can be carried out. As a preferable process of producing the novel protein of the present invention, a method of expressing the protein in a filamentous fungus belonging to Hyphomycetes is provided. As preferable filamentous fungi which may be used as a host in the present invention, there may be mentioned, for example, filamentous fungi belonging to genus *Trichoderma*, *Humicola*, *Aspergillus*, *Acremonium*, or *Penicillium*, more preferably *Trichoderma* or *Humicola*. More particularly, there may be mentioned, for example, *Trichoderma viride*, *Trichoderma reesei*, *Trichoderma longibrachiatum*, *Humicola insolens*, *Humicola thermoidea*, *Aspergillus niger*, *Aspergillus oryzae*, *Acremonium cellulolyticus*, or *Penicillium pinophilum*, preferably *Trichoderma viride* or *Humicola insolens*.

Use of Cellulase/Cellulase Preparation

The present invention relates to a cellulase preparation comprising the protein of the present invention (for example, a protein comprising the amino acid sequence of SEQ ID NO: 4 or a partial sequence thereof, a modified protein thereof, or a protein obtainable by cultivating the host cell of the present invention).

Conventionally, the cellulase preparation may contain, for example, fillers (for example, lactose, sodium chloride, or sorbitol), antiseptics, and/or nonionic surfactants, in addition to the cellulase enzyme. The form of the cellulase preparation may be solid or liquid, such as powder, particulate, granule, non-dusting granule, or liquid formulation. In addition to the protein of the present invention, the cellulase preparation of the present invention may contain other cellulase enzymes, such as cellobiohydrolase, $\beta$-gulucosidase, and/or endoglucanase other than the endoglucanase of the present invention. The non-dusting granule (preferably a granule not having a dustability), that is one form of cellulase preparation, can be produced according to the common dry granulation method. That is, a powder protein of the present invention is mixed with one or plural substances selected from the group comprising inorganic salts (such as sodium sulfate or sodium chloride), minerals (such as bentonite or montmorillonite), and organic substances (such as starch or grinded cellulose). Thereafter, the powders or the finely suspended suspension of one or plural nonionic surfactants are added to the mixture, and then the obtained product is fully mixed or kneaded. Depending on the situation, a synthetic polymer (such as polyethylene glycol) or a natural polymer (such as starch), which binds solids, is optionally added to the mixture and further kneaded. Thereafter, granulation is carried out by extrusion molding, using, for example, a disk pelleter, and the obtained molded material is then converted into a spherical form using a marumerizer followed by drying, so that non-dusting granules can be produced. The amount of one or plural nonionic surfactants is not particularly limited, and is preferably 0.1 to 50% by weight, more preferably 0.1 to 30% by weight, most preferably 1 to 10% by weight of the total weight of the cellulase preparation of the present invention. It is also possible to coat the surface of granules with a polymer or the like to control the permeation of oxygen or water. Further, the liquid preparation, which is one of the cellulase preparations (preferably a stabilized liquid), can be prepared by blending an endoglucanase stabilizer (such as a synthetic or natural polymer) with a solution containing the protein of the present invention and, if necessary, adding inorganic salts and/or a synthetic preservative.

In this case, one or plural nonionic surfactants can be blended with the liquid preparation. The amount of one or plural of the nonionic surfactants is not particularly limited, and is preferably 0.1 to 50% by weight, more preferably 0.1 to 30% by weight, most preferably 1 to 10% by weight of the total amount of the cellulase preparation of the present invention. Further, the present invention provides a detergent composition comprising the protein of the present invention or the cellulase preparation of the present invention. The detergent composition of the present invention may also comprise surfactants, which may be anionic, nonionic, cationic, amphoteric, or zwitterionic, or a mixture thereof. The detergent composition may comprise other detergent compositions known in the art, for example, a builder, bleach, bleaching agent, tarnish inhibitor, sequestant, soil releasing polymer, flavor, other enzymes (such as protease, lipase, or amylase), stabilizer for enzyme, granulater, optical brightner, and/or foaming agent. As typical anionic surfactants, there may be mentioned, for example, linear alkyl benzene sulfonate (LAS), alkyl sulphate (AS), α-olefin sulfonate (AOS), polyoxyethylene alkylether sulfonate (AES), α-sulfo fatty acid ester (α-SFMe), or alkali metal salts of naturally-occurring fatty acid. As the nonion surfactants, there may be mentioned, for example, polyoxyethylene alkyl ether (AE), alkylpolyethylene glycol ether, nonylphenol polyethylene glycol ether, fatty acid methyl ester ethoxylate, sucrose, or fatty acid ester of glucose, or esters of alkylglucoside or polyethoxylated alkylglucoside.

The method of the present invention for treating a cellulose-containing fabric is carried out by bringing the cellulose-containing fabric into contact with the protein of the present invention, the cellulase preparation of the present invention, or the detergent composition of the invention. The following properties of cellulose-containing fabric can be improved by the method of the present invention:
(1) Improvement of the touch feel and appearance of a fabric by reducing weight;
(2) Providing a localized color change to a colored cellulose-containing fabric, that is, providing a stonewash-like appearance and texture to a colored cellulose-containing fabric, typically denim;
(3) Color clarification of a colored cellulose-containing fabric;
(4) Softening of a fabric (reduction of the rate of stiffness, and a reduction of stiffness); and
(5) Removal of fuzz (reduction of the rate of the formation of fuzz, and reduction of fuzz.

More particularly, the method of the present invention can be carried out by adding the protein of the present invention, the cellulase preparation of the present invention, or the detergent composition of the present invention into water in which a fabric is or will be soaked, for example, during a soaking, washing, or rinsing of a fabric. Conditions such as contact temperature or the amount of the protein, the cellulase preparation, or the detergent composition to be added may be appropriately determined in accordance with various other conditions. For example, for improvement of the touch feel and appearance of a cellulose-containing fabric by reducing weight, the protein, the cellulase preparation, or the detergent composition in a protein concentration of 0.1 to 50 mg/L is preferably used at a temperature of approximately 10 to 60° C. For providing a localized color change to a colored cellulose-containing fabric, the protein, the cellulase preparation, or the detergent composition in a protein concentration of 0.1 to 100 mg/L is preferably used at a temperature of approximately 20 to 60° C. For color clarification of a colored cellulose-containing fabric, the protein, the cellulase preparation, or the detergent composition in a protein concentration of 0.01 to 20 mg/L is preferably used at a temperature of approximately 10 to 60° C. For reducing the stiffness of a cellulose-containing fabric or reducing the rate of the formation of stiffness, the protein, the cellulase preparation, or the detergent composition in a protein concentration of 0.01 to 20 mg/L is preferably used at a temperature of 10 to 60° C. For reduction of fuzz from a cellulose-containing fabric or reduction of the rate of the formation of fuzz, the protein, the cellulase preparation, or the detergent composition in a protein concentration of 0.01 to 20 mg/L is preferably used at a temperature of 10 to 60° C.

Further, the present invention relates to a method for deinking waste paper, characterized by using the protein of the present invention or the cellulase preparation of the present invention, in the process of treating the waste paper together with a deinking agent. The protein or the cellulase preparation of the present invention is useful in the process of producing recycled paper from waste paper, since an efficiency of the deinking can be improved by reacting waste paper therewith. According to the deinking method, the whiteness of waste paper can be remarkably improved by reducing residual-ink fiber. The deinking agent is not particularly limited, so long as it is agent which can be used in deinking waste paper in general. As the deinking agent, there may be mentioned, for example, alkalis (such as sodium hydroxide or sodium carbonate), sodium silicate, hydrogen peroxide, phosphates, anionic or nonionic surfactants, scavengers such as oleic acid, and assistant agents such as a pH stabilizer, a chelating agent, or a dispersing agent. Waste paper which can be treated by the deinking method is not particularly limited, so long as it is common waste paper. As the waste paper, there may be mentioned, used newspaper, used magazine paper, and low to middle grade printed used paper which comprises mechanical pulp and chemical pulp; used wood-free paper comprising chemical pulp; or printed waste paper thereof such as coating paper. A paper other than the common waste paper can be treated by the deinking method, so long as it deposits ink.

Further, the present invention relates to a method for improving a water freeness of paper pulp, which comprises the process of treating a paper pulp with the protein of the present invention or the cellulase preparation of the present invention. According to the method, it is considered that this method can significantly improve a water freeness of paper pulp, without a serious decline of strength. A paper pulp which can be treated by the method is not particularly limited, but there may be mentioned, for example, waste paper pulp, recycled paperboard pulp, kraft pulp, sulfite pulp, thermo-mechanical treatment pulp, and other high-yield pulp.

The present invention relates to a method for improving a digestibility of animal feed, comprising the step of treating the animal feed with the protein of the present invention or the cellulase preparation of the present invention. According to this method, a digestibility of animal feed can be improved by digesting glucan in animal feed into appropriate molecules having a low molecular weight. Further, a digestibility of glucan in animal feed can be improved by using the protein of the present invention in animal feed. According to the present invention, a method for improving a digestibility of animal feed, comprises the step of treating the animal feed with the protein of the present invention or the cellulase preparation of the present invention, is provided.

The present invention relates to a method of producing biomass ethanol, comprising the step of treating a cellulose-based substance (such as cellulose fibers) with the protein or the cellulase preparation of the present invention. According to the method, the cellulose-based substance may be digested and saccharified by treating the substance with the protein of the present invention, to produce glucose. The resulting glucose may be converted into biomass ethanol by fermentation techniques using other microorganisms such as yeasts.

Deposition of Microorganisms

*Penicillium pinophilum* PF1365, from which the endoglucanase PPCE of the present invention was derived, was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2007, and the international deposit number is FERM BP-10780.

*Escherichia coli* JM109/p28FULL18 of the present invention, i.e., *Escherichia coli* JM109 transformed with plasmid p28FULL18 obtained by inserting the PPCE gene into plasmid PCR 2.1-TOPO, was internationally deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2007, and the international deposit number is FERM BP-10781.

*Trichoderma viride* MC300-1, which may be used as a host for the expression vector of the present invention, was domestically (originally) deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Sep. 9, 1996, and was transferred to an international deposit on Aug. 11, 1997. The international deposit number (a number in parenthesis [ ] following the international deposit number is a domestic deposit number) is FERM BP-6047 [FERM P-15842].

EXAMPLES

The present invention now will be further illustrated by, but is by no means limited to, the following Example.

Example 1

Isolation and Purification of Component having Activity to Remove Fuzz from Colored Cotton from *Penicillium Pinophilum* PF1365

*Penicillium pinophilum* PF1365 was cultivated in a TS medium (2.0% soluble starch, 1.0% glucose, 0.5% polypeptone, 0.6% wheat germ, 0.3% yeast extract, 0.2% soybean cake, 0.2% calcium carbonate, pH 7.0) at 25° C. under shaking. After cultivation for 24 hours, the fungus was inoculated into an (N) medium (5.0% avicel, 2.0% yeast extract, 0.1% polypeptone, 0.03% magnesium sulfate, pH6.8), and further cultivated at 25° C. for 5 days. The mycelia were removed from the culture to obtain a culture supernatant as a crude cellulase preparation solution. Ammonium sulfate was added to the crude cellulase preparation solution so that a final concentration of ammonium sulfate in the solution became 1.2 mol/L. The solution was applied to a HiTrap™ Phenyl HP column (GE Healthcare Bio-Sciences) equilibrated with a 50 mM sodium acetate buffer (pH 5) containing 1.2 mol/L ammonium sulfate, and eluted by a stepwise elution method using 1.2 mol/L, 0.96 mol/L, 0.72 mol/L, 0.48 mol/L, 0.24 mol/L, and 0 mol/L ammonium sulfate in a 50 mmol/L sodium acetate buffer (pH 5), to collect fractions. The fraction eluted at an ammonium sulfate concentration of 0.24 mol/L exhibited an activity of removing fuzz from a colored cotton fabric. The activity of removing fuzz from a colored cotton fabric was evaluated by the following procedure. Cotton knit fabrics stained blue were treated in a large washer to generate fuzz. The blue cotton knit fabrics with fuzz were treated under the following conditions for removing fuzz and the fuzz-removing activity evaluated, by judging the extent of fuzz removed from fabrics after the treatment on the basis of a visual evaluation.

Testing machine: Launder Meter L-12 (Daiei Kagaku Seiki MFG., Japan)
Temperature: 40° C.
Time: 120 minutes
Reaction pH: pH 2 (5 mmol/L citrate buffer)
To a treating solution, an appropriate amount of stainless beads were added together with each fraction solution.

The fraction eluted at an ammonium sulfate concentration of 0.24 mol/L was desalted using a PD-10 desalting column (GE Healthcare Bio-Sciences) in accordance with the conditions described in an attached manual, and adjusted to become a 50 mmol/L acetate buffer (pH 4.0). The adjusted fraction was applied to a Resource Mono S column (GE Healthcare Bio-Sciences) equilibrated with a 50 mmol/L acetate buffer (pH 4.0), and eluted by a stepwise elution method from a 50 mmol/L sodium acetate buffer (pH 4.0) to a 50 mmol/L sodium acetate buffer (pH 5.0) containing 1 mol/L sodium chloride, in increments of 0.1 mol NaCl, to collect fractions. As a result, the activity of removing fuzz from a colored cotton fabric was detected in the fraction that passed through the column without being adsorbed by the column. This flow-through fraction was applied to a Resource Mono Q column (GE Healthcare Bio-Sciences) equilibrated with a 50 mmol/L acetate buffer (pH 4.0), and eluted by a stepwise elution method from a 50 mmol/L acetate buffer (pH 4.0) to a 50 mmol/L acetate buffer (pH 5.0) containing 1 mol/L sodium chloride, in increments of 0.1 mol NaCl, to collect fractions. As a result, the activity of removing fuzz from a colored cotton fabric was detected in the fraction that passed through the column without being adsorbed by the column. The resulting flow-through fraction was concentrated using a 10 kDa cut-off ultrafiltration membrane (Millipore) to designate a PPCE fraction. This PPCE fraction exhibited a CMCase activity. Next, the crude cellulase preparation solution and active fractions obtained in the above column purification steps were subjected to SDS-PAGE. This SDS-PAGE was carried out using an electrophoresis apparatus Safety Cell Mini STC-808 (Tefco) and a Precast Mini Gel 12%-SDS-PAGEmini, 1.0 mm in gel thickness (Tefco) in accordance with protocols attached thereto. LMW Calibration For SDS Electrophoresis (GE Healthcare Bio-Sciences) was used as molecular markers. After the electrophoresis, the gel was stained with Coomassie brilliant blue R-250 (Nacalai Tesque), and decolorized. As a result, it was found that a protein having an average molecular weight (MW) of approximately 26 kDa was gradually concentrated by each purification step. In particular, the content of the protein of approximately 26 kDa was remarkably increased in the PPCE fraction, by comparison with the crude cellulase preparation solution. From these results, we presumed that the component having the activity to remove fuzz from a colored cotton fabric was the protein having an average molecular weight (MW) of approximately 26 kDa, and carried out the following experiments.

Example 2

Identification of N-Terminal Amino Acid Sequence of PPCE Derived from *Penicillium Pinophilum* PF1365

The PPCE fraction obtained in Example 1 was subjected to SDS-PAGE, and electrically blotted onto a PVDF membrane (Millipore) using Multiphor II (GE Healthcare Bio-Sciences). The membrane was stained with Brilliant Blue G (Tokyo Chemical Industry Co., Ltd.), and decolorized. From the membrane, the portion on which a protein (PPCE) having a molecular weight of approximately 26 kDa was blotted was excised. This piece was subjected to a protein sequencer Model 492 (Applied Biosystems) to determine the N-terminal amino acid sequence, but no signals from Edman degradation were detected. It was revealed from this result that the N-terminal amino acid was protected by modification.

The excised membrane was immersed in a 0.5% polyvinylpyrrolidone-40 (Sigma)/100 mmol/L acetic acid solution at 37° C. for 30 minutes to block protein-unbound portions on the membrane, and treated with Pfu pyroglutamate aminopeptidase (Takara Bio) at 50° C. for 5 hours to remove the modified N-terminal residue from the protein. The resulting membrane was resubjected to the protein sequencer to obtain the following amino acid sequence. Xaa is an unknown amino acid residue.

Result of sequencing: Gln-Ser-Leu-Xaa-Ser-Gln-Tyr-Ser-Ser-Tyr-Thr-Ser (12 residues) (SEQ ID NO: 1)

Since signals were obtained by treating the protected N-terminal amino acid with Pfu pyroglutamate aminopeptidase, it is considered that the N-terminal amino acid of PPCE is pyroglutamic acid (pyroGlu). Further, Xaa is presumed to be cysteine (Cys), because a signal derived from cysteine is not detectable with this protein sequencer. Therefore, the N-terminal amino acid sequence of PPCE is considered the following sequence.

N-terminal amino acid sequence of PPCE: Gln-Gln-Ser-Leu-Cys-Ser-Gln-Tyr-Ser-Ser-Tyr-Thr-Ser (13 residues; The N-terminal Gln is modified into pyroGlu.) (SEQ ID NO: 2)

When this N-terminal amino acid sequence was used to carry out a homology search (GENETYX; GENETYX Corporation), this sequence showed a homology with the amino acid sequence of endoglucanase III (RU 2238974) derived from *Penicillium verruculosum*. This result suggested that PPCE was an endoglucanase belonging to family 12.

Example 3

PCT Amplification of Endoglucanase PPCE Gene

Since the N-terminal amino acid sequence of PPCE had a homology with that of endoglucanase III derived from *Penicillium verruculosum* belonging to family 12, we attempted to amplify an endoglucanase PPCE gene derived from *Penicillium pinophilum* PF1365 by PCR on the basis of the nucleotide sequence of EG III described in RU 2238974.

(1) Isolation of Chromosomal DNA Derived from *Penicillium Pinophilum* PF1365

*Penicillium pinophilum* PF1365 was cultivated in the TS medium at 28° C. for 24 hours, and centrifuged to collect mycelia. A kit (ISOPLANT; Nippon Gene Co., Ltd.) was used to extract chromosomal DNA from the obtained mycelia. The extraction was carried out in accordance with the conditions described in the manual attached thereto.

(2) Amplification of Family 12 Endoglucanase Gene Fragment Derived from *Penicillium Pinophilum* PF1365 by PCR Synthetic primers having the following sequences were prepared on the basis of the N-terminal and C-terminal amino acid sequences of endoglucanase III derived from *Penicillium verruculosum*.

```
MSW-N:
                                            (SEQ ID NO: 5)
CAACAGAGTCTATGCGCTCAATACTCGAGCTACACCAGT

MSW-C:
                                            (SEQ ID NO: 6)
CTAATTGACAGCTGCAGACCAA
```

A PCR reaction was carried out using the above primers (MSW-N, MSW-C), the chromosomal DNA prepared in Example 3(1) as the template, and an LA PCR™ Kit Ver2.1 (Takara Bio). This PCR reaction was carried out by performing a reaction at 94° C. for 1 minute, repeating a cycle consisting of a reaction at 94° C. for 30 seconds, a reaction at 60° C. for 30 seconds, and a reaction at 72° C. for 1 minute 20 times, and performing a reaction at 72° C. for 10 minutes. The resulting reaction liquid was subjected to agarose gel electrophoresis. As a result, it was confirmed that a gene fragment of approximately 0.8 kbp was amplified, and thus, we attempted to clone this fragment to determine the nucleotide sequence thereof. The gene fragment of approximately 0.8 kbp, which was isolated by agarose gel electrophoresis, was excised from the gel, and a Wizard SVGel and PCR Clean-Up System (Promega) was used to purify the DNA. The purification was carried out in accordance with the conditions described in the manual attached thereto. The resulting purified DNA of approximately 0.8 kbp was cloned into a TOPO vector (PCR 2.1-TOPO) using a TOPO TA Cloning Kit (Invitrogen). The resulting plasmid was amplified and extracted to determine the DNA sequence thereof in accordance with conventional procedures. This extraction of the plasmid was carried out using a QIAfilter Plasmid Kit (Xiagen) in accordance with the conditions described in the manual attached thereto. The nucleotide sequence of the DNA was determined by a reaction using a dRhodamine Terminator Kit (Applied Biosystems) and the M13 universal primer or a Rev primer having the following sequence as a primer.

```
Rev:
CAGGAAACAGCTATGAC          (SEQ ID NO: 7)
```

This reaction was carried out in accordance with the conditions described in the manual attached thereto. The resulting reaction liquid was purified in accordance with the conditions described in the manual attached thereto, and analyzed using an ABI PRISM 310 Genetic Analyzer (Applied Biosystems). As a result, the gene fragment amplified by PCR was a gene having a homology with endoglucanase III derived from *Penicillium verruculosum*.

Example 4

Cloning of Gene Fragment of family 12 Endoglucanase Derived from *Penicillium Pinophilum* PF1365 by Genome Walking We attempted to amplify the upstream and downstream regions of the PCR-amplified gene fragment of family 12 endoglucanase derived from *Penicillium pinophilum* PF1365 using a GenomeWalker kit (Becton, Dickinson and Company). This amplification was carried out in accordance with the conditions described in the manual attached thereto. Chromosomal DNA extracted from *Penicillium pinophilum* PF1365 was completely digested with restriction enzyme PvuII or StuI, and the resulting digested fragments of chromosomal DNA were ligated to an adaptor attached to the kit to construct PvuII and StuI libraries. In addition, synthetic primers having the following sequences were prepared on the basis of the sequence determined in Example 3 to use PCR reactions described below.

```
24-GSP-R1:
CGCCAGAGCTGGAAATGGAGTTGACATAAG    (SEQ ID NO: 8)

24-GSP-R2:
GTGCACTGGGAGCCAGAGCCACTGCTCTCA    (SEQ ID NO: 9)

24-GSP-F1:
TTTCGTATGATCTCTTCACGGCAGCGGATA    (SEQ ID NO: 10)

24-GSP-F2:
ATCAACCATGTTACCTACAGTGGTGACTAT    (SEQ ID NO: 11)
```

A PCR reaction was carried out by using the PvuII or StuI library as the template, the 24-GSP-R1 or 24-GSP-F1 primer and an AP-1 primer attached to the kit, and Ex Taq Premix (Takara Bio). This PCR reaction was carried out by performing a reaction at 94° C. for 2 minutes, repeating a cycle consisting of a reaction at 94° C. for 2 seconds and a reaction at 72° C. for 3 minutes 7 times, repeating a cycle consisting of a reaction at 94° C. for 2 seconds and a reaction at 67° C. for 3 minutes 32 times, and performing a reaction at 67° C. for 4 minutes. The PCR reaction liquid obtained by the first PCR reaction was diluted with deionized water, and the second PCR reaction was carried out by using the diluted liquid as the template, the 24-GSP-R2 or 24-GSP-F2 primer and an AP-2 primer attached to the kit, and Ex Taq Premix (Takara Bio). This PCR reaction was carried out by performing a reaction at 94° C. for 2 minutes, repeating a cycle consisting of a reaction at 94° C. for 2 seconds and a reaction at 72° C. for 3 minutes 5 times, repeating a cycle consisting of a reaction at 94° C. for 2 seconds and a reaction at 67° C. for 3 minutes 20 times, and performing a reaction at 67° C. for 4 minutes. The resulting reaction liquid was subjected to agarose gel electrophoresis. As a result, it was confirmed that a gene fragment of approximately 2 kbp was amplified in the sample obtained by using the PvuII library as the template, performing the first PCR reaction using the 24-GSP-R1 primer and the AP-1 primer, and performing the second PCR reaction using the 24-GSP-R2 primer and the AP-2 primer. Further, it was confirmed that a gene fragment of approximately 2 kbp was amplified in the sample obtained by using the StuI library as the template, performing the first PCR reaction using the 24-GSP-F1 primer and the AP-1 primer, and performing the second PCR reaction using the 24-GSP-F2 primer and the AP-2 primer. These gene fragments of approximately 2 kbp were excised from the gels, and a QIAQUICK GEL EXTRACTION KIT (Xiagen) was used to purify the DNAs. The purification was carried out in accordance with the conditions described in the manual attached thereto. The resulting purified DNAs of approximately 2 kbp were individually cloned into a TOPO vector (PCR 2.1-TOPO) using a TOPO PCR CLONING KIT (Invitrogen).

The resulting plasmids were amplified and purified to determine the DNA sequences thereof in accordance with conventional procedures. This purification of the plasmids was carried out using a QIAPREP MINIPREP KIT (Xiagen) in accordance with the conditions described in the manual attached thereto. The nucleotide sequences of the DNAs were determined by a reaction using a dRhodamine Terminator Kit (Applied Biosystems) and the M13 universal primer or the Rev primer as a primer. This reaction was carried out in accordance with the conditions described in the manual attached thereto. The resulting reaction liquids were purified in accordance with the conditions described in the manual attached thereto, and analyzed using an ABI PRISM 310 Genetic Analyzer (Applied Biosystems).

As a result, the PCR product of approximately 2 kbp derived from the PvuII library contained the upstream region of the gene obtained in Example 3(2), and the PCR product of approximately 2 kbp derived from the StuI library contained the downstream region of the gene obtained in Example 3(2). These nucleotide sequences of the PCR products were linked to determine the full length of the nucleotide sequence of the PPCE gene derived from *Penicillium pinophilum* PF1365. The determined nucleotide sequence of the PPCE gene (SEQ ID NO: 3) contained a region homologous with the coding region of the endoglucanase III gene derived from *Penicillium verruculosum*. The homology between these genes calculated using a commercially available Genetic Information Processing Software GENETYX (GENETYX Corporation) was 82%. The homology of the amino acid sequence (SEQ ID NO: 4) deduced from the nucleotide sequence of the DNA fragment PPCE with that of endoglucanase III derived from *Penicillium verruculosum* was calculated using the GENETYX (GENETYX Corporation) as 86%. A blastp search, based on the amino acid sequence (SEQ ID NO: 4) deduced from the nucleotide sequence of the DNA fragment, was carried out against the known database NCBI to find that it had a homology of 72% with that of FI-CMCase derived from *Aspergollus aculeatus* and a homology of 53% with that of EG III derived from *Trichoderma reesei*. Because all of these proteins were endoglucanases belonging to family 12, it was considered that the obtained DNA fragment was a gene fragment containing the coding region of a family 12 endoglucanase gene derived from *Penicillium pinophilum* PF1365 and the upstream and downstream regions thereof.

Example 5

Expression of PPCE Gene in *Trichoderma viride*

(1) Cloning Gene Fragment for PPCE Expression

The following primers for mutagenesis having the StuI recognition site upstream of the initiation codon and the PstI recognition site downstream of the stop codon were designed, and the PPCE gene was amplified by PCR.

```
32228-NSTU:
                                   (SEQ ID NO: 12)
CCAGGCCTGCGCATCATGAAGCTAACTTTTCTCCTG

32228-CPST:
                                   (SEQ ID NO: 13)
CCCTGCAGCTAATTGACAGAAGCAGACC
```

This PCR reaction was carried out using the chromosomal DNA of *Penicillium pinophilum* PF1365 obtained in Example 3(1) as the template, synthetic DNA primers 32228-NSTU and 32228-CPST, and Ex Taq Premix (Takara Bio), by performing a reaction at 94° C. for 2 minutes, repeating a cycle consisting of a reaction at 94° C. for 1 minute, a reaction at 50° C. for 2 minutes, and a reaction at 72° C. for 1.5 minutes 25 times, and performing a reaction at 72° C. for 3 minutes. The sample after the reaction was subjected to agarose gel electrophoresis, and a gene fragment of approximately 800 bp was excised and purified using a QIAQUICK GEL EXTRACTION KIT (Xiagen) in accordance with the conditions described in the manual attached thereto. The resulting purified DNA was cloned into a TOPO vector (PCR 2.1-TOPO) using a TOPO PCR CLONING KIT (Invitrogen). The resulting plasmid was designated p28FULL18. Plasmid p28FULL18 was amplified and purified in accordance with conventional procedures, to determine the DNA sequence thereof as described above. As a result, it was confirmed that plasmid p28FULL18 contained the PPCE gene having the StuI recognition site upstream of the initiation codon and the PstI recognition site downstream of the stop codon. The nucleotide sequence of the PPCE gene contained in plasmid p28FULL18 accorded with the nucleotide sequence of the PPCE coding region determined in Example 4, and thus, this gene fragment was used in the following procedures to express the PPCE gene.

(2) Construction of Plasmid for Expressing PPCE

Plasmid p28FULL18 was digested with restriction enzymes StuI and PstI, and the sample after the reaction was subjected to agarose gel electrophoresis. The gene fragment of approximately 800 bp was excised from the gel, and a QIAQUICK GEL EXTRACTION KIT (Xiagen) was used to purify the DNA. Plasmid pCBI-M2 (Example B1 of WO 2005/056787) was digested with restriction enzymes StuI and PstI, and the sample after the reaction was subjected to agarose gel electrophoresis. A gene fragment of approximately 5.6 kbp was excised from the gel, and a QIAQUICK GEL EXTRACTION KIT (Xiagen) was used to purify the DNA. This gene fragment of approximately 5.6 kbp was ligated to the previously-obtained gene fragment of approximately 800 bp using a TaKaRa DNA Ligation Kit Ver.1 (Takara Bio) to construct plasmid pPPCE-F2.

(3) Preparation of *Trichoderma Viride* Transformant with Plasmid pPPCE-F2

*Trichoderma viride* was transformed with plasmid pPPCE-F2 obtained in Example 5(2) in accordance with the procedures described in WO 2005/056787. That is, this transformation was carried out by a co-transformation method using *Trichoderma viride* strain 2 deficient in a gene for uracil biosynthesis (pyr4) as a host and a pyr4 gene of *Neurospora crassa* as a selection marker. More particularly, in accordance with the method described in WO 2005/056787, protoplasts of *Trichoderma viride* strain 2 were prepared, and 100 μL of the protoplast suspension was mixed with 7 μg of plasmid pPPCE-F2 and 3 μg of plasmid pPYR4 (a plasmid prepared by subcloning the pyr4 gene of *Neurospora crassa* into LITMUS28). After this mixture was allowed to stand on ice for 5 minutes, 400 μL of a PEG solution (60% polyethylene glycol 4000, 10 mmol/L calcium chloride, and 10 mmol/L Tris-HCL buffer, pH7.5) was added to the mixture, and allowed to stand on ice for 20 minutes. The resulting protoplast suspension was washed with an SUTC buffer (0.5 mol/L sucrose, 10 mmol/L calcium chloride, and 10 mmol/L Tris-HCl buffer, pH 7.5), overlaid with soft agar on a minimum medium containing 0.5 mol/L sucrose, and cultivated at 28° C. for 5 days. After the cultivation, grown colonies were transferred on the minimum medium, and colonies grown on this medium were used as transformants in the following procedures.

(4) Cultivation of *Trichoderma Viride* Transformant with Plasmid pPPCE-F2

From the transformants obtained in Example 5(3), 50 strains were inoculated into a PSW medium (1.0% glucose, 4.0% lactose, 2.0% soybean cake, 1.0% wheat germ, 0.2% potassium dihydrogen phosphate, 0.2% ammonium sulfate, 0.2% ammonium phosphate, 0.2% calcium carbonate) and cultivated at 28° C. for 5 days. After the cultivation, mycelia were removed by centrifugation to obtain culture supernatants as crude enzyme solutions. These crude enzyme solutions were subjected to SDS-PAGE, and it was confirmed that a protein of approximately 26 kDa was specifically expressed in the transformants. The culture supernatant of strain 322F-205, which most highly expressed the protein, was used to carry out the following washing test.

Example 6

Evaluation of Fuzz-Removing Activity in Strain Expressing PPCE Gene (1) Measurement of Expressed Protein Concentration To evaluate a fuzz-removing activity of the strain expressing the PPCE gene, each gene of EG III derived from *Trichoderma reesei* (non-patent reference 1), SCE3 derived from *Trichoderma viride* (patent reference 5), and FI-CMCase derived from *Aspergollus aculeatus* (non-patent reference 2) was expressed in *Trichoderma viride*, and culture supernatants thereof were prepared, as controls, in accordance with the procedures described in Example 5. These culture supernatants for controls, and the culture supernatant of the strain expressing the PPCE gene were subjected to SDS-PAGE using a 12% gel in accordance with the procedures described in Example 1. After the electrophoresis, the gel was stained using a SYPRO Ruby protein gel stain (Invitrogen) and washed with water. Bands were analyzed using a Molecular Imager FX (Bio-Rad Laboratories) and a Quantity One (Bio-Rad Laboratories) to determine a ratio of the expressed protein to the total proteins. Further, a concentration of total proteins contained in each culture supernatant was assayed using bovine γ globulin as a standard and a Protein Assay Kit (Bio-Rad Laboratories). The concentration of the expressed protein was calculated by multiplying the concentration of total proteins by the ratio of the expressed protein.

TABLE 1

Amount of expressed protein in Trichoderma transformants

| Active protein | Concentration of total proteins | Ratio of expressed protein | Concentration of expressed protein |
|---|---|---|---|
| PPCE (present invention) | 13.2 μg/mL | 6.1% | 0.81 μg/mL |
| EG III | 11.8 μg/mL | 18.1% | 2.1 μg/mL |
| SCE3 | 14.7 μg/mL | 17.9% | 2.6 μg/mL |
| FI-CMCase | 13.3 μg/mL | 9.8% | 1.3 μg/mL |

(2) Measurement of Fuzz-Removing Activity from Colored Cotton

The culture supernatants from the PPCE-expressed strain and the control strains prepared in Example 6(1) were used to measure the fuzz-removing activity thereof. More particularly, cotton knit fabrics stained brown were treated in a large washer to generate fuzz. The brown cotton knit fabrics with fuzz were treated under the following conditions for removing fuzz and the fuzz-removing activity evaluated, by judging the extent of fuzz removed from fabrics after the treatment on the basis of a visual evaluation.

Testing machine: Launder Meter L-12 (Daiei Kagaku Seiki MFG., Japan)
Temperature: 40° C.
Time: 60 minutes
Reaction solution: 5 mmol/L acetate buffer (pH 4) 40 mL
To a treating solution, an appropriate amount of stainless beads were added together with each culture supernatant.

Volumes of culture supernatants required to remove approximately 50% of the formed fuzz on the basis of a visual evaluation are shown in Table 2. Amounts of the expressed protein used to remove 50% of the fuzz were also calculated from the expressed protein concentrations determined in Example 6(1). As a result, it was clarified that PPCE required the least protein to remove fuzz from fabrics.

TABLE 2

Fuzz-removing activity in PPCE-expressed strain

| Active protein | Volume of culture supernatant removing 50% of fuzz | Amount of expressed protein removing 50% of fuzz |
|---|---|---|
| PPCE (present invention) | 100 μL | 0.081 μg |
| EG III | 140 μL | 0.29 μg |
| SCE3 | 150 μL | 0.39 μg |
| FI-CMCase | 200 μL | 0.26 μg |

Example 7

Temperature and pH Profiles in Fuzz-Removing Activity of PPCE (1) Temperature Profile in Fuzz-Removing Activity of PPCE The culture supernatants of the PPCE- and EG III-expressed strains used in Example 6 were used to examine temperature profiles under the following conditions for washing. After the washing treatment, extents of fuzz removed from fabrics were judged on the basis of a visual evaluation, and volumes of culture supernatants required to remove approximately 50% of fuzz on the basis of a visual evaluation were calculated. Relative activities were determined from the volumes, when the activity at the temperature showing the highest fuzz-removing activity in each sample was regarded as 100%. As shown in Table 3, the optimum temperature of PPCE was 30° C., and that of EG III was 40° C.

Testing machine: Launder Meter L-12 (Daiei Kagaku Seiki MFG., Japan)
Temperature: 20° C. to 60° C.
Time: 60 minutes
Reaction solution: 5 mmol/L acetate buffer (pH 4) 40 mL
To a treating solution, an appropriate amount of stainless beads were added together with each culture supernatant.

TABLE 3

Temperature profile of PPCE-expressed strain

| Reaction temperature | PPCE (present invention) Relative activity (%) | EG III Relative activity (%) |
|---|---|---|
| 20° C. | 80 | 75 |
| 30° C. | 100 | 85 |
| 40° C. | 95 | 100 |
| 50° C. | 80 | 80 |
| 60° C. | 40 | 50 |

(2) pH Profile in Fuzz-Removing Activity of PPCE

The culture supernatants of the PPCE- and EG III-expressed strains used in Example 6 were used to examine pH profiles under the following conditions for washing. After the washing treatment, extents of fuzz removed from fabrics were judged on the basis of a visual evaluation, and volumes of culture supernatants required to remove approximately 50% of fuzz on the basis of a visual evaluation were calculated. Relative activities were determined from the volumes, when the activity at the pH showing the highest fuzz-removing activity in each sample was regarded as 100%. As shown in Table 4, the optimum pH of PPCE was pH 3, and that of EG III was pH 4.

Testing machine: Launder Meter L-12 (Daiei Kagaku Seiki MFG., Japan)
Temperature: 40° C.
Time: 60 minutes
Reaction solution: 5 mmol/L citrate buffer or acetate buffer (pH 2 to 6) 40 mL
To a treating solution, an appropriate amount of stainless beads were added together with each culture supernatant.

TABLE 4 pH profile of PPCE-expressed strain

| Buffer, pH | PPCE Washing activity (%) | EG III Washing activity (%) |
|---|---|---|
| Citrate, pH 2 | 85 | 25 |
| Citrate, pH 3 | 100 | 45 |
| Citrate, pH 4 | 90 | 100 |
| Acetate, pH 4 | 90 | 90 |
| Acetate, pH 5 | 30 | 55 |
| Acetate, pH 6 | 10 or less | 10 |

Example 8

Expression of Codon-Optimized PPCE Gene in *Trichoderma viride*

(1) Cloning of Codon-Optimized PPCE Gene

A PPCE gene consisting only of codons highly used in genus *Trichoderma* was synthesized by PCR reactions.
a) Preparation of PCEM1-2 Fragment
Two synthetic oligonucleotides having the following sequences were prepared.

PCEM-1:
(SEQ ID NO: 14)
CCAGGCCTGCGCATCATGAAGCTGACCTTCCTGCTGAACCTGGCCGTCGC
CGCCAGCGCCCAGCAGAGCCTGTGCAGCCAGTACAGCAGCTACAC

PCEM-2:
(SEQ ID NO: 15)
TGGCTGCCGCTGCCGCTGCTCTCGCCCCACAGGTTGTTGTTGACGCTGTA
CTGGCCGCTGGTGTAGCTGCTGTACTGGCT

A PCR reaction was carried out using 20 pmol of the above primers (PCEM-1 and PCEM-2) and Primestar MAX DNA POLYMERASE (Takara), in the absence of a template, by repeating a cycle consisting of a reaction at 98° C. for 10 seconds, a reaction at 55° C. for 5 seconds, and a reaction at 72° C. for 30 seconds 30 times. The resulting DNA was purified from the reaction liquid using a QIAQUICK PCR PURIFICATION KIT (Xiagen), and eluted into 50 μL of a TE buffer, in accordance with the conditions described in the manual attached thereto. The resulting DNA fragment of approximately 150 bp was designated PCEM1-2.
b) Preparation of PCEM3-4 Fragment
Two synthetic oligonucleotides having the following sequences were prepared.

PCEM-3:
(SEQ ID NO: 16)
AGCAGCGGCAGCGGCAGCCAGTGCACCTACGTCAACAGCATCAGCAGCAG
CGGCGTCAGCTGGAGCACCACCTGGAACTG

PCEM-4:
(SEQ ID NO: 17)
TTGGTCAGGCCGCTCAGCTGGCTGTTGGCGTAGCTCTTGACGCTGGTGCT
GCCGCCGCTCCAGTTCCAGGTGGTGCTCCA

A PCR reaction using 20 pmol of the above primers (PCEM-3 and PCEM-4) was carried out in the absence of a template, and the resulting fragment was purified, in accordance with the procedures described in Example 8(1)a). The resulting DNA fragment of approximately 140 bp was designated PCEM3-4.

c) Preparation of PCEM5-6 Fragment

Two synthetic oligonucleotides having the following sequences were prepared.

PCEM-5:
(SEQ ID NO: 18)
CAGCTGAGCGGCCTGACCAAGAAGCTGGTCAGCAACCTGCAGAGCATCCC
CACCAGCGTCCAGTGGAGCTACAGCAACAC

PCEM-6:
(SEQ ID NO: 19)
GTGACGTGGTTGATGTCGGCGGCGGTGAACAGGTCGTAGCTGACGTCGGC
GACGATGTTGGTGTTGCTGTAGCTCCACTG

A PCR reaction using 20 pmol of the above primers (PCEM-5 and PCEM-6) was carried out in the absence of a template, and the resulting fragment was purified, in accordance with the procedures described in Example 8(1)a). The resulting DNA fragment of approximately 140 bp was designated PCEM5-6.

d) Preparation of PCEM7-8 Fragment

Two synthetic oligonucleotides having the following sequences were prepared.

PCEM-7:
(SEQ ID NO: 20)
GCCGACATCAACCACGTCACCTACAGCGGCGACTACGAGCTGATGATCTG
GTAAATATGCCCCCGTCGTATTTCAAGTAT

PCEM-8:
(SEQ ID NO: 21)
CAGGGGCTGGGCGCCGCCGTACTTGCCCAGCCTGATATCTTGATTAGCGG
GAGATGTCTCACTTGAAATACGACGGGG

A PCR reaction using 20 pmol of the above primers (PCEM-7 and PCEM-8) was carried out in the absence of a template, and the resulting fragment was purified, in accordance with the procedures described in Example 8(1)a). The resulting DNA fragment of approximately 140 bp was designated PCEM7-8.

e) Preparation of PCEM9-10 Fragment

Two synthetic oligonucleotides having the following sequences were prepared.

PCEM-9:
(SEQ ID NO: 22)
ACGGCGGCGCCCAGCCCCTGGGCAGCCAGATCGGCACCGCCAACGTCGGC
GGCGCCACCTGGCAGCTGTGGTACGGCGTC

PCEM-10:
(SEQ ID NO: 23)
GCCGTTCCAGCTGGTGGTCTGGCTGCTGGCGACGAAGCTGTAGGTCTTCT
GGCTGCCGTTGACGCCGTACCACAGCTGCC

A PCR reaction using 20 pmol of the above primers (PCEM-9 and PCEM-10) was carried out in the absence of a template, and the resulting fragment was purified, in accordance with the procedures described in Example 8(1)a). The resulting DNA fragment of approximately 140 bp was designated PCEM9-10.

f) Preparation of PCEM11-12 Fragment

Two synthetic oligonucleotides having the following sequences were prepared.

PCEM-11:
(SEQ ID NO: 24)
AGACCACCAGCTGGAACGGCGACATCCTGCAGTTCTTCAAGTACCTGCAG
AGCAACCAGGGCTTCCCCGCCAGCAGCCAG

PCEM-12:
(SEQ ID NO: 25)
ATCATGTCAGATACAAGGAGTCTATAGGAACAGAAAGGGTCATGGCTTAC
CGATCAGGTACTGGCTGCTGGCGGGGAAGC

A PCR reaction using 20 pmol of the above primers (POEM-11 and PCEM-12) was carried out in the absence of a template, and the resulting fragment was purified, in accordance with the procedures described in Example 8(1)a). The resulting DNA fragment of approximately 140 bp was designated PCEM11-12.

g) Preparation of PCEM13-14 Fragment

Two synthetic oligonucleotides having the following sequences were prepared.

PCEM-13:
(SEQ ID NO: 26)
CTCCTTGTATCTGACATGATTGCTTCGGTATCAGACCTGCAGTTCGGCAC
CGAGCCCTTCACCGGCAGCCAGACCACCCT

PCEM-14:
(SEQ ID NO: 27)
CCCTCGAGCTAGTTGACGCTGGCGCTCCAGTGGTTGACGGTCAGGGTGGT
CTGGCTGCCGGT

A PCR reaction using 20 pmol of the above primers (PCEM-13 and POEM-14) was carried out in the absence of a template, and the resulting fragment was purified, in accordance with the procedures described in Example 8(1)a). The resulting DNA fragment of approximately 120 bp was designated PCEM13-14.

h) Preparation of PCEM1-4 Fragment

A second PCR reaction was carried out using 1 µL of PCEM1-2 obtained in Example 8(1)a) and 1 µL of PCEM3-4 obtained in Example 8(1)b) as templates, 20 µmol of the above primers (PCEM-1 and PCEM-4), and Primestar MAX DNA POLYMERASE (Takara), by repeating a cycle consisting of a reaction at 98° C. for 10 seconds, a reaction at 55° C. for 5 seconds, and a reaction at 72° C. for 30 seconds 30 times. The resulting DNA was purified from the reaction liquid using a QIAQUICK PCR PURIFICATION KIT (Xiagen), and eluted into 50 µl of a TE buffer. The resulting DNA fragment of approximately 270 bp was designated PCEM1-4.

i) Preparation of PCEM5-8 Fragment

A second PCR reaction was carried out using 1 µL of PCEM5-6 obtained in Example 8(1)c) and 1 µL of PCEM7-8 obtained in Example 8(1)d) as templates, and 20 pmol of the above primers (PCEM-5 and PCEM-8). This PCR reaction and a purification of the resulting fragment were carried out in accordance with the procedures described in Example 8(1)h) to designate the resulting DNA fragment of approximately 260 bp as PCEM5-8.

j) Preparation of PCEM9-12 Fragment

A second PCR reaction was carried out using 1 µL of PCEM9-10 obtained in Example 8(1)e) and 1 µL of PCEM11-12 obtained in Example 8(1)f) as templates, and 20 pmol of the above primers (PCEM-9 and PCEM-12). This PCR reaction and a purification of the resulting fragment were carried out in accordance with the procedures described in Example 8(1)h) to designate the resulting DNA fragment of approximately 260 bp as PCEM9-12.

k) Preparation of PCEM1-8 Fragment

A third PCR reaction was carried out using 1 µL of PCEM1-4 obtained in Example 8(1)h) and 1 µl of PCEM5-8 obtained in Example 8(1)i) as templates, 20 pmol of the above primers (PCEM-1 and PCEM-8), and Primestar MAX DNA POLYMERASE (Takara), by repeating a cycle consisting of a reaction at 98° C. for 10 seconds, a reaction at 55° C. for 5 seconds, and a reaction at 72° C. for 30 seconds 30 times. The resulting DNA was purified from the reaction liquid using a QIAQUICK PCR PURIFICATION KIT (Xiagen), and eluted into 50 µL of a TE buffer. The resulting DNA fragment of approximately 510 bp was designated PCEM1-8.

1) Preparation of CEM9-14 Fragment

A third PCR reaction was carried out using 1 µL of PCEM9-12 obtained in Example 8(1)j) and 1 µL of PCEM13-14 obtained in Example 8(1)g) as templates, and 20 pmol of the above primers (PCEM-9 and PCEM-14). This PCR reaction and a purification of the resulting fragment were carried out in accordance with the procedures described in Example 8(1)k) to designate the resulting DNA fragment of approximately 360 bp as PCEM9-14.

m) Preparation of Plasmid pCR-PCEm

A fourth PCR reaction was carried out using 1 µL of PCEM1-8 obtained in Example 8(1)k) and 1 µL of PCEM9-14 obtained in Example 8(1)l) as templates, and 20 pmol of the above primers (PCEM-1 and PCEM-14), by repeating a cycle consisting of a reaction at 98° C. for 10 seconds, a reaction at 55° C. for 5 seconds, and a reaction at 72° C. for 30 seconds 30 times. The sample after the reaction was subjected to agarose gel electrophoresis. A gene fragment of approximately 800 bp was excised from the gel, purified using a QIAQUICK GEL EXTRACTION KIT (Xiagen), and eluted into a 50 µL of a TE buffer. A buffer, dNTPs, and EXTaq (Takara) were added to the resulting purified DNA, and incubated at 72° C. for 10 minutes to add the A bases to the DNA. The treated DNA was cloned into a TOPO vector (PCR 2.1-TOPO) using a TOPO PCR CLONING KIT (Invitrogen) to designate the obtained plasmid as pCR-PCEm. Plasmid pCR-PCEm was amplified and purified in accordance with conventional methods, and the DNA sequence thereof was analyzed in accordance with the procedures described above. As a result, it was confirmed that plasmid pCR-PCEm contained not only the coding region (SEQ ID NO: 28) of a codon-optimized PPCE gene, but also the StuI recognition site upstream of the initiation codon and the XhoI recognition site downstream of the stop codon.

(2) Construction of Plasmid for Expressing Codon-Optimized PPCE

Plasmid pCR-PCEm was digested with restriction enzymes StuI and XhoI, and the sample after the reaction was subjected to agarose gel electrophoresis. The separated gene fragment of approximately 800 bp was excised from the gel, and a QIAQUICK GEL EXTRACTION KIT (Xiagen) was used to purify the DNA.

Plasmid pCBI-M2 was digested with restriction enzymes StuI and XhoI, and a gene fragment of approximately 5.6 kbp was collected and purified, in a similar fashion as described in Example 5(2). The previously obtained gene fragment of approximately 800 bp was ligated to this gene fragment of approximately 5.6 kbp using Ligation High (TOYOBO) to prepare plasmid pPPCE-M.

(3) Preparation of *Trichoderma Viride* Transformant with Plasmid pPPCE-M

*Trichoderma viride* was transformed with plasmid pPPCE-M obtained in Example 8(2). That is, this transformation was carried out by a co-transformation method using *Trichoderma viride* strain 2 deficient in a gene for uracil biosynthesis (pyr4) as a host and a pyr4 gene of *Neurospora crassa* as a selection marker, in accordance with the procedures described in Example 5(3). *Trichoderma viride* strain 2 was transformed with 7 µg of plasmid pPPCE-M and 3 µg of plasmid pPYR4 to obtain 40 strains of transformants.

(4) Cultivation of *Trichoderma Viride* Transformant with Plasmid pPPCE-M

From the transformants obtained in Example 8(3), 40 strains were inoculated into the PSW medium described in Example 5(4), and cultivated at 28° C. for 5 days. After the cultivation, mycelia were removed by centrifugation to obtain culture supernatants as crude enzyme solutions. These crude enzyme solutions were subjected to SDS-PAGE, and it was confirmed that a protein of approximately 26 kDa was specifically expressed in the transformants. Further, these crude enzyme solutions were used to measure the fuzz-removing activity thereof in accordance with Example 7 (conditions for measurement: temperature=30° C., time=60 minutes, reaction solution=5 mmol/L citrate buffer, pH 3.0), and it was confirmed that the activity was specifically improved in the transformants by comparison with the untransformed host.

INDUSTRIAL APPLICABILITY

The present invention is useful for various treatments for cellulose, for example, in treating a cellulose-containing fabric, deinking waste paper, improving a water freeness of paper pulp, improving a digestibility of animal feed, and producing bioethanol.

Although the present invention has been described with reference to specific embodiments, various changes and modifications obvious to those skilled in the art are possible without departing from the scope of the appended claims.

Free Text in Sequence Listing

Each sequence of SEQ ID NOS: 5 to 27 in the Sequence Listing is a primer for PCR. The sequence of SEQ ID NO: 28 is a codon optimized (modified) gene. The sequence of SEQ ID NO: 29 is an amino acid sequence deduced from the codon optimized (modified) gene.

The invention claimed is:

1. An isolated protein selected from the group consisting of the following proteins (a) to (d):
   (a) a protein comprising the amino acid sequence of residues 16-236 of SEQ ID NO: 4,
   (b) a protein comprising the amino acid sequence of SEQ ID NO: 4,
   (c) a protein comprising the amino acid sequence of residues 16-236 of SEQ ID NO: 4, wherein the N-terminal glutamine residue is converted to a pyroglutamic acid residue by modification, and
   (d) a protein comprising an amino acid sequence having at least 90% amino acid sequence identity to the amino acid sequence of residues 16-236 or residues 1-236 of SEQ ID NO: 4, or comprising an amino acid sequence having at least 90% amino acid sequence identity to the amino acid sequence of residues 16-236 of SEQ ID NO: 4 and wherein the N-terminal glutamine residue is converted to a pyroglutamic acid residue by modification, and having an endoglucanase activity.

2. An isolated polynucleotide encoding the protein of claim 1.

3. An isolated polynucleotide which comprises the nucleotide sequence of SEQ ID NO: 3 or 28, or which consists of nucleotides 46-834 of SEQ ID NO: 3 or 28.

4. An expression vector comprising the polynucleotide of claim 2.

5. An isolated host cell transformed with the expression vector of claim 4.

6. The host cell of claim 5, wherein the host is a yeast or a filamentous fungus.

7. The host cell of claim 6, wherein the filamentous fungus is a microorganism belonging to genus *Trichoderma, Humicola, Aspergillus, Acremonium*, or *Penicillium*.

8. The host cell of claim 7, wherein the filamentous fungus is a microorganism belonging to genus *Trichoderma*.

9. The host cell of claim 8, wherein the filamentous fungus is *Trichoderma viride*.

10. A process for producing the protein of claim 1, comprising the steps of:
    cultivating host cells transformed with an expression vector comprising a polynucleotide encoding the protein, and
    collecting the protein from the host cells or a culture obtained by the cultivation.

11. A protein produced by the process of claim 10.

12. A cellulase preparation comprising the protein of claim 1.

13. A detergent composition comprising:
    (a) the protein of claim 1; or
    (b) a cellulase preparation comprising the protein of (a).

14. A method of treating a cellulose-containing fabric, comprising the step of bringing the cellulose-containing fabric into contact with:
    (a) the protein of claim 1,
    (b) a cellulase preparation comprising the protein of (a), or
    (c) a detergent composition comprising the protein of (a) or the cellulase preparation of (b).

15. A method of reducing weight to improve the touch feel and appearance of a cellulose-containing fabric, comprising the step of bringing the cellulose-containing fabric into contact with:
    (a) the protein of claim 1,
    (b) a cellulase preparation comprising the protein of (a), or
    (c) a detergent composition comprising the protein of (a) or the cellulase preparation of (b).

16. A method of providing a localized color change to a colored cellulose-containing fabric, comprising the step of bringing the colored cellulose-containing fabric into contact with:
    (a) the protein of claim 1,
    (b) a cellulase preparation comprising the protein of (a), or
    (c) a detergent composition comprising the protein of (a) or the cellulase preparation of (b).

17. A method of color clarification of a colored cellulose-containing fabric, comprising the step of bringing the colored cellulose-containing fabric into contact with:
    (a) the protein of claim 1,
    (b) a cellulase preparation comprising the protein of (a), or
    (c) a detergent composition comprising the protein of (a) or the cellulase preparation of (b).

18. A method of reducing fuzzing of a cellulose-containing fabric or reducing a rate of the formation of fuzz, comprising the step of bringing the cellulose-containing fabric into contact with:
    (a) the protein of claim 1,
    (b) a cellulase preparation comprising the protein of (a), or
    (c) a detergent composition comprising the protein of (a) or the cellulase preparation of (b).

19. A method of reducing stiffness of a cellulose-containing fabric or reducing a rate of the formation of stiffness, comprising the step of bringing the cellulose-containing fabric into contact with:
    (a) the protein of claim 1,
    (b) a cellulase preparation comprising the protein of (a), or
    (c) a detergent composition comprising the protein of (a) or the cellulase preparation of (b).

20. The method of claim 14, wherein the contacting step is carried out by soaking, washing, or rinsing the fabric.

21. A method of deinking waste paper, comprising treating waste paper together with a deinking agent, and either (a) the protein of claim 1 or (b) a cellulase preparation comprising the protein of (a).

22. A method of improving a water freeness of paper pulp, comprising the step of treating the paper pulp with either (a) the protein of claim 1 or (b) a cellulase preparation comprising the protein of (a).

23. A method of improving a digestibility of animal feed, comprising the step of treating the animal feed with either (a) the protein of claim 1 or (b) a cellulase preparation comprising the protein of (a).

24. A method of producing biomass ethanol by digesting and saccharifying a cellulose-based substance, comprising the step of treating the cellulose-based substance with either (a) the protein of claim 1 or (b) a cellulase preparation comprising the protein of (a).

* * * * *

SEQUENCE LISTING

```
<160> NUMBER OF SEQ ID NOS: 30

<210> SEQ ID NO 1
<211> LENGTH: 12
<212> TYPE: PRT
<213> ORGANISM: Penicillium pinophilum PF1365
<220> FEATURE:
<221> NAME/KEY: MISC_FEATURE
<222> LOCATION: (4)..(4)
<223> OTHER INFORMATION: Xaa is deduced to be cystein residue which
      was not determined by protein sequencer.
```

-continued

```
<400> SEQUENCE: 1

Gln Ser Leu Xaa Ser Gln Tyr Ser Ser Tyr Thr Ser
1               5                   10

<210> SEQ ID NO 2
<211> LENGTH: 13
<212> TYPE: PRT
<213> ORGANISM: Penicillium pinophilum PF1365
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

Gln Gln Ser Leu Cys Ser Gln Tyr Ser Ser Tyr Thr Ser
1               5                   10

<210> SEQ ID NO 3
<211> LENGTH: 834
<212> TYPE: DNA
<213> ORGANISM: Penicillium pinophilum PF1365
<220> FEATURE:
<221> NAME/KEY: CDS
<222> LOCATION: (1)..(410)
<220> FEATURE:
<221> NAME/KEY: CDS
<222> LOCATION: (470)..(690)
<220> FEATURE:
<221> NAME/KEY: CDS
<222> LOCATION: (755)..(831)
<220> FEATURE:
<221> NAME/KEY: exon
<222> LOCATION: (1)..(410)
<220> FEATURE:
<221> NAME/KEY: sig_peptide
<222> LOCATION: (1)..(45)
<220> FEATURE:
<221> NAME/KEY: Intron
<222> LOCATION: (411)..(469)
<220> FEATURE:
<221> NAME/KEY: exon
<222> LOCATION: (470)..(690)
<220> FEATURE:
<221> NAME/KEY: Intron
<222> LOCATION: (691)..(754)
<220> FEATURE:
<221> NAME/KEY: exon
<222> LOCATION: (755)..(831)

<400> SEQUENCE: 3 atg aag cta act ttt ctc ctg aac ctg gcc gtt gcc gca tct gct cag      48
Met Lys Leu Thr Phe Leu Leu Asn Leu Ala Val Ala Ala Ser Ala Gln
1               5                   10                  15 cag agc cta tgc tct caa tac tcg agc tac acc agt ggc cag tac tcc      96
Gln Ser Leu Cys Ser Gln Tyr Ser Ser Tyr Thr Ser Gly Gln Tyr Ser
            20                  25                  30 gtc aac aac aac cta tgg ggt gag agc agt ggc tct ggc tcc cag tgc     144
Val Asn Asn Asn Leu Trp Gly Glu Ser Ser Gly Ser Gly Ser Gln Cys
        35                  40                  45 act tat gtc aac tcc att tcc agc tct ggc gtt tca tgg tct act acc     192
Thr Tyr Val Asn Ser Ile Ser Ser Ser Gly Val Ser Trp Ser Thr Thr
    50                  55                  60 tgg aac tgg tcc gga ggc agc acc tcg gtc aag agc tat gcc aat tcg     240
Trp Asn Trp Ser Gly Gly Ser Thr Ser Val Lys Ser Tyr Ala Asn Ser
65                  70                  75                  80 cag ttg agt ggc ctc acc aag aag ctc gtc agc aac ttg caa agc att     288
Gln Leu Ser Gly Leu Thr Lys Lys Leu Val Ser Asn Leu Gln Ser Ile
                85                  90                  95 cct acc tct gtg cag tgg agc tat agc aat acc aac atc gtt gcc gat     336
```

```
Pro Thr Ser Val Gln Trp Ser Tyr Ser Asn Thr Asn Ile Val Ala Asp
            100                 105                 110 gtt tcg tat gat ctc ttc acg gca gcg gat atc aac cat gtt acc tac    384
Val Ser Tyr Asp Leu Phe Thr Ala Ala Asp Ile Asn His Val Thr Tyr
            115                 120                 125 agt ggt gac tat gag ctc atg atc tg  gtaaatatgc ccccgtcgta          430
Ser Gly Asp Tyr Glu Leu Met Ile Trp
130                 135 tttcaagtat gagacatctc ccgctaatca agatatcag g ctc ggt aag tac ggc   485
                                            Leu Gly Lys Tyr Gly
                                                            140 ggt gcc cag ccc ctc ggc agt caa atc gga aca gcc aac gtg gga ggc    533
Gly Ala Gln Pro Leu Gly Ser Gln Ile Gly Thr Ala Asn Val Gly Gly
            145                 150                 155 gca acc tgg cag ctg tgg tat ggc gta aac gga tcc caa aaa acg tac    581
Ala Thr Trp Gln Leu Trp Tyr Gly Val Asn Gly Ser Gln Lys Thr Tyr
            160                 165                 170 agt ttc gtc gcc tcc agc caa aca act tca tgg aac ggc gat atc ttg    629
Ser Phe Val Ala Ser Ser Gln Thr Thr Ser Trp Asn Gly Asp Ile Leu
175                 180                 185                 190 cag ttc ttc aag tat cta cag agc aac cag ggc ttt cca gct agc agc    677
Gln Phe Phe Lys Tyr Leu Gln Ser Asn Gln Gly Phe Pro Ala Ser Ser
                195                 200                 205 cag tac ttg atc g gtaagccatg acccttttctg ttcctataga ctccttgtat    730
Gln Tyr Leu Ile
            210 ctgacatgat tgcttcggta tcag at  ctg caa ttc ggc acg gaa ccg ttt    780
                              Asp Leu Gln Phe Gly Thr Glu Pro Phe
                                              215 aca gga agc cag act act ttg acg gtc aac cat tgg tct gct tct gtc    828
Thr Gly Ser Gln Thr Thr Leu Thr Val Asn His Trp Ser Ala Ser Val
220                 225                 230                 235 aat tag                                                            834
Asn

<210> SEQ ID NO 4
<211> LENGTH: 236
<212> TYPE: PRT
<213> ORGANISM: Penicillium pinophilum PF1365

<400> SEQUENCE: 4

Met Lys Leu Thr Phe Leu Leu Asn Leu Ala Val Ala Ala Ser Ala Gln
1               5                   10                  15

Gln Ser Leu Cys Ser Gln Tyr Ser Tyr Thr Ser Gly Gln Tyr Ser
            20                  25                  30

Val Asn Asn Leu Trp Gly Glu Ser Gly Ser Gly Ser Gln Cys
            35                  40                  45

Thr Tyr Val Asn Ser Ile Ser Ser Gly Val Ser Trp Ser Thr Thr
            50                  55                  60

Trp Asn Trp Ser Gly Gly Ser Thr Ser Val Lys Ser Tyr Ala Asn Ser
65                  70                  75                  80

Gln Leu Ser Gly Leu Thr Lys Lys Leu Val Ser Asn Leu Gln Ser Ile
                85                  90                  95

Pro Thr Ser Val Gln Trp Ser Tyr Ser Asn Thr Asn Ile Val Ala Asp
            100                 105                 110

Val Ser Tyr Asp Leu Phe Thr Ala Ala Asp Ile Asn His Val Thr Tyr
            115                 120                 125

Ser Gly Asp Tyr Glu Leu Met Ile Trp Leu Gly Lys Tyr Gly Gly Ala
130                 135                 140
```

```
Gln Pro Leu Gly Ser Gln Ile Gly Thr Ala Asn Val Gly Gly Ala Thr
145                 150                 155                 160

Trp Gln Leu Trp Tyr Gly Val Asn Gly Ser Gln Lys Thr Tyr Ser Phe
                165                 170                 175

Val Ala Ser Ser Gln Thr Thr Ser Trp Asn Gly Asp Ile Leu Gln Phe
            180                 185                 190

Phe Lys Tyr Leu Gln Ser Asn Gln Gly Phe Pro Ala Ser Ser Gln Tyr
        195                 200                 205

Leu Ile Asp Leu Gln Phe Gly Thr Glu Pro Thr Gly Ser Gln Thr
    210                 215                 220

Thr Leu Thr Val Asn His Trp Ser Ala Ser Val Asn
225                 230                 235

<210> SEQ ID NO 5
<211> LENGTH: 39
<212> TYPE: DNA
<213> ORGANISM: artificial sequence
<220> FEATURE:
<223> OTHER INFORMATION: Description of Artificial Sequence: A primer
      for PCR (MSW-N)

<400> SEQUENCE: 5
caacagagtc tatgcgctca atactcgagc tacaccagt                              39

<210> SEQ ID NO 6
<211> LENGTH: 22
<212> TYPE: DNA
<213> ORGANISM: artificial sequence
<220> FEATURE:
<223> OTHER INFORMATION: Description of Artificial Sequence: A primer
      for PCR (MSW-C)

<400> SEQUENCE: 6
ctaattgaca gctgcagacc aa                                                22

<210> SEQ ID NO 7
<211> LENGTH: 17
<212> TYPE: DNA
<213> ORGANISM: artificial sequence
<220> FEATURE:
<223> OTHER INFORMATION: Description of Artificial Sequence: A primer
      for PCR (Rev)

<400> SEQUENCE: 7
caggaaacag ctatgac                                                      17

<210> SEQ ID NO 8
<211> LENGTH: 30
<212> TYPE: DNA
<213> ORGANISM: artificial sequence
<220> FEATURE:
<223> OTHER INFORMATION: Description of Artificial Sequence: A primer
      for PCR (24-GSP-R1)

<400> SEQUENCE: 8
cgccagagct ggaaatggag ttgacataag                                        30

<210> SEQ ID NO 9
<211> LENGTH: 30
<212> TYPE: DNA
<213> ORGANISM: artificial sequence
<220> FEATURE:
<223> OTHER INFORMATION: Description of Artificial Sequence: A primer
      for PCR (24-GSP-R2)
```

-continued

<400> SEQUENCE: 9
gtgcactggg agccagagcc actgctctca                                30

<210> SEQ ID NO 10
<211> LENGTH: 30
<212> TYPE: DNA
<213> ORGANISM: artificial sequence
<220> FEATURE:
<223> OTHER INFORMATION: Description of Artificial Sequence: A primer
      for PCR (24-GSP-F1)

<400> SEQUENCE: 10
tttcgtatga tctcttcacg gcagcggata                                30

<210> SEQ ID NO 11
<211> LENGTH: 30
<212> TYPE: DNA
<213> ORGANISM: artificial sequence
<220> FEATURE:
<223> OTHER INFORMATION: Description of Artificial Sequence: A primer
      for PCR (24-GSP-F2)

<400> SEQUENCE: 11
atcaaccatg ttacctacag tggtgactat                                30

<210> SEQ ID NO 12
<211> LENGTH: 36
<212> TYPE: DNA
<213> ORGANISM: artificial sequence
<220> FEATURE:
<223> OTHER INFORMATION: Description of Artificial Sequence: A primer
      for PCR (32228-NSTU)

<400> SEQUENCE: 12
ccaggcctgc gcatcatgaa gctaactttt ctcctg                         36

<210> SEQ ID NO 13
<211> LENGTH: 28
<212> TYPE: DNA
<213> ORGANISM: artificial sequence
<220> FEATURE:
<223> OTHER INFORMATION: Description of Artificial Sequence: A primer
      for PCR (32228-CPST)

<400> SEQUENCE: 13
ccctgcagct aattgacaga agcagacc                                  28

<210> SEQ ID NO 14
<211> LENGTH: 95
<212> TYPE: DNA
<213> ORGANISM: artificial sequence
<220> FEATURE:
<223> OTHER INFORMATION: Description of Artificial Sequence: A primer
      for PCR (PCEM-1)

<400> SEQUENCE: 14
ccaggcctgc gcatcatgaa gctgaccttc ctgctgaacc tggccgtcgc cgccagcgcc    60
cagcagagcc tgtgcagcca gtacagcagc tacac                              95

<210> SEQ ID NO 15
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-2)

```
<400> SEQUENCE: 15
tggctgccgc tgccgctgct ctcgccccac aggttgttgt tgacgctgta ctggccgctg      60
gtgtagctgc tgtactggct                                                  80

<210> SEQ ID NO 16
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-3)

<400> SEQUENCE: 16
agcagcggca gcggcagcca gtgcacctac gtcaacagca tcagcagcag cggcgtcagc      60
tggagcacca cctggaactg                                                  80

<210> SEQ ID NO 17
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-4)

<400> SEQUENCE: 17
ttggtcaggc cgctcagctg gctgttggcg tagctcttga cgctggtgct gccgccgctc      60
cagttccagg tggtgctcca                                                  80

<210> SEQ ID NO 18
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-5)

<400> SEQUENCE: 18
cagctgagcg gcctgaccaa gaagctggtc agcaacctgc agagcatccc caccagcgtc      60
cagtggagct acagcaacac                                                  80

<210> SEQ ID NO 19
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-6)

<400> SEQUENCE: 19
gtgacgtggt tgatgtcggc ggcggtgaac aggtcgtagc tgacgtcggc gacgatgttg      60
gtgttgctgt agctccactg                                                  80

<210> SEQ ID NO 20
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-7)

<400> SEQUENCE: 20
gccgacatca accacgtcac ctacagcggc gactacgagc tgatgatctg gtaaatatgc      60
ccccgtcgta tttcaagtat                                                  80
```

```
<210> SEQ ID NO 21
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-8)

<400> SEQUENCE: 21
caggggctgg gcgccgccgt acttgcccag cctgatatct tgattagcgg gagatgtctc      60
atacttgaaa tacgacgggg                                                 80

<210> SEQ ID NO 22
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-9)

<400> SEQUENCE: 22
acggcggcgc ccagcccctg ggcagccaga tcggcaccgc caacgtcggc ggcgccacct      60
ggcagctgtg gtacggcgtc                                                 80

<210> SEQ ID NO 23
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-10)

<400> SEQUENCE: 23
gccgttccag ctggtggtct ggctgctggc gacgaagctg taggtcttct ggctgccgtt      60
gacgccgtac cacagctgcc                                                 80

<210> SEQ ID NO 24
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-11)

<400> SEQUENCE: 24
agaccaccag ctggaacggc gacatcctgc agttcttcaa gtacctgcag agcaaccagg      60
gcttccccgc cagcagccag                                                 80

<210> SEQ ID NO 25
<211> LENGTH: 80
<212> TYPE: DNA
<213> ORGANISM: artificial sequence
<220> FEATURE:
<223> OTHER INFORMATION: Description of Artificial Sequence: A primer
      for PCR (PCEM-12)

<400> SEQUENCE: 25
atcatgtcag atacaaggag tctataggaa cagaaagggt catggcttac cgatcaggta      60
ctggctgctg gcggggaagc                                                 80

<210> SEQ ID NO 26
<211> LENGTH: 80
<212> TYPE: DNA
```

<213> ORGANISM: artificial sequence
<220> FEATURE:
<223> OTHER INFORMATION: Description of Artificial Sequence: A primer
      for PCR (PCEM-13)

<400> SEQUENCE: 26
ctccttgtat ctgacatgat tgcttcggta tcagacctgc agttcggcac cgagcccttc      60
accggcagcc agaccaccct                                                  80

<210> SEQ ID NO 27
<211> LENGTH: 62
<212> TYPE: DNA
<213> ORGANISM: artificial sequence
<220> FEATURE:
<223> OTHER INFORMATION: Description of Artificial Sequence: A primer
      for PCR (PCEM-14)

<400> SEQUENCE: 27
ccctcgagct agttgacgct ggcgctccag tggttgacgg tcagggtggt ctggctgccg      60
gt                                                                     62

<210> SEQ ID NO 28
<211> LENGTH: 834
<212> TYPE: DNA
<213> ORGANISM: artificial sequence
<220> FEATURE:
<223> OTHER INFORMATION: Description of Artificial Sequence: Codon
      optimized (modified) gene
<220> FEATURE:
<221> NAME/KEY: CDS
<222> LOCATION: (1)..(410)
<220> FEATURE:
<221> NAME/KEY: CDS
<222> LOCATION: (470)..(690)
<220> FEATURE:
<221> NAME/KEY: CDS
<222> LOCATION: (755)..(831)
<220> FEATURE:
<221> NAME/KEY: exon
<222> LOCATION: (1)..(410)
<220> FEATURE:
<221> NAME/KEY: sig_peptide
<222> LOCATION: (1)..(45)
<220> FEATURE:
<221> NAME/KEY: Intron
<222> LOCATION: (411)..(469)
<220> FEATURE:
<221> NAME/KEY: exon
<222> LOCATION: (470)..(690)
<220> FEATURE:
<221> NAME/KEY: Intron
<222> LOCATION: (691)..(754)
<220> FEATURE:
<221> NAME/KEY: exon
<222> LOCATION: (755)..(831)

<400> SEQUENCE: 28 atg aag ctg acc ttc ctg ctg aac ctg gcc gtc gcc gcc agc gcc cag      48
Met Lys Leu Thr Phe Leu Leu Asn Leu Ala Val Ala Ala Ser Ala Gln
1               5                   10                  15 cag agc ctg tgc agc cag tac agc agc tac acc agc ggc cag tac agc      96
Gln Ser Leu Cys Ser Gln Tyr Ser Ser Tyr Thr Ser Gly Gln Tyr Ser
            20                  25                  30 gtc aac aac aac ctg tgg ggc gag agc agc ggc agc ggc agc cag tgc     144
Val Asn Asn Asn Leu Trp Gly Glu Ser Ser Gly Ser Gly Ser Gln Cys
        35                  40                  45 acc tac gtc aac agc atc agc agc agc ggc gtc agc tgg agc acc acc     192
Thr Tyr Val Asn Ser Ile Ser Ser Ser Gly Val Ser Trp Ser Thr Thr
    50                  55                  60

```
tgg aac tgg agc ggc ggc agc acc agc gtc aag agc tac gcc aac agc      240
Trp Asn Trp Ser Gly Gly Ser Thr Ser Val Lys Ser Tyr Ala Asn Ser
 65                  70                  75                  80 cag ctg agc ggc ctg acc aag aag ctg gtc agc aac ctg cag agc atc      288
Gln Leu Ser Gly Leu Thr Lys Lys Leu Val Ser Asn Leu Gln Ser Ile
                 85                  90                  95 ccc acc agc gtc cag tgg agc tac agc aac acc aac atc gtc gcc gac      336
Pro Thr Ser Val Gln Trp Ser Tyr Ser Asn Thr Asn Ile Val Ala Asp
            100                 105                 110 gtc agc tac gac ctg ttc acc gcc gcc gac atc aac cac gtc acc tac      384
Val Ser Tyr Asp Leu Phe Thr Ala Ala Asp Ile Asn His Val Thr Tyr
        115                 120                 125 agc ggc gac tac gag ctg atg atc tg  gtaaatatgc cccgtcgta             430
Ser Gly Asp Tyr Glu Leu Met Ile Trp
    130                 135 tttcaagtat gagacatctc ccgctaatca agatatcag g ctg ggc aag tac ggc     485
                                            Leu Gly Lys Tyr Gly
                                                            140 ggc gcc cag ccc ctg ggc agc cag atc ggc acc gcc aac gtc ggc ggc      533
Gly Ala Gln Pro Leu Gly Ser Gln Ile Gly Thr Ala Asn Val Gly Gly
                145                 150                 155 gcc acc tgg cag ctg tgg tac ggc gtc aac ggc agc cag aag acc tac      581
Ala Thr Trp Gln Leu Trp Tyr Gly Val Asn Gly Ser Gln Lys Thr Tyr
160                 165                 170 agc ttc gtc gcc agc agc cag acc acc agc tgg aac ggc gac atc ctg      629
Ser Phe Val Ala Ser Ser Gln Thr Thr Ser Trp Asn Gly Asp Ile Leu
175                 180                 185                 190 cag ttc ttc aag tac ctg cag agc aac cag ggc ttc ccc gcc agc agc      677
Gln Phe Phe Lys Tyr Leu Gln Ser Asn Gln Gly Phe Pro Ala Ser Ser
                195                 200                 205 cag tac ctg atc g gtaagccatg acccttctg ttcctataga ctccttgtat         730
Gln Tyr Leu Ile
            210 ctgacatgat tgcttcggta tcag ac  ctg cag ttc ggc acc gag ccc ttc       780
                              Asp Leu Gln Phe Gly Thr Glu Pro Phe
                                              215 acc ggc agc cag acc acc ctg acc gtc aac cac tgg agc gcc agc gtc      828
Thr Gly Ser Gln Thr Thr Leu Thr Val Asn His Trp Ser Ala Ser Val
220                 225                 230                 235 aac tag                                                              834
Asn

<210> SEQ ID NO 29
<211> LENGTH: 236
<212> TYPE: PRT
<213> ORGANISM: artificial sequence
<220> FEATURE:
<223> OTHER INFORMATION: Description of Artificial Sequence: Amino
      acid sequence deduced from codon optimized (modified) gene

<400> SEQUENCE: 29

Met Lys Leu Thr Phe Leu Leu Asn Leu Ala Val Ala Ala Ser Ala Gln
1               5                   10                  15

Gln Ser Leu Cys Ser Gln Tyr Ser Tyr Thr Ser Gly Gln Tyr Ser
            20                  25                  30

Val Asn Asn Asn Leu Trp Gly Glu Ser Gly Ser Gly Ser Gln Cys
        35                  40                  45

Thr Tyr Val Asn Ser Ile Ser Ser Ser Gly Val Ser Trp Ser Thr Thr
    50                  55                  60

Trp Asn Trp Ser Gly Gly Ser Thr Ser Val Lys Ser Tyr Ala Asn Ser
65                  70                  75                  80
```

Gln Leu Ser Gly Leu Thr Lys Lys Leu Val Ser Asn Leu Gln Ser Ile
                85                  90                  95

Pro Thr Ser Val Gln Trp Ser Tyr Ser Asn Thr Asn Ile Val Ala Asp
            100                 105                 110

Val Ser Tyr Asp Leu Phe Thr Ala Ala Asp Ile Asn His Val Thr Tyr
            115                 120                 125

Ser Gly Asp Tyr Glu Leu Met Ile Trp Leu Gly Lys Tyr Gly Gly Ala
            130                 135                 140

Gln Pro Leu Gly Ser Gln Ile Gly Thr Ala Asn Val Gly Gly Ala Thr
145                 150                 155                 160

Trp Gln Leu Trp Tyr Gly Val Asn Gly Ser Gln Lys Thr Tyr Ser Phe
                165                 170                 175

Val Ala Ser Ser Gln Thr Thr Ser Trp Asn Gly Asp Ile Leu Gln Phe
            180                 185                 190

Phe Lys Tyr Leu Gln Ser Asn Gln Gly Phe Pro Ala Ser Ser Gln Tyr
            195                 200                 205

Leu Ile Asp Leu Gln Phe Gly Thr Glu Pro Phe Thr Gly Ser Gln Thr
            210                 215                 220

Thr Leu Thr Val Asn His Trp Ser Ala Ser Val Asn
225                 230                 235

<210> SEQ ID NO 30
<211> LENGTH: 221
<212> TYPE: PRT
<213> ORGANISM: Penicillium pinophilum PF1365
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 30

Gln Gln Ser Leu Cys Ser Gln Tyr Ser Ser Tyr Thr Ser Gly Gln Tyr
1               5                   10                  15

Ser Val Asn Asn Asn Leu Trp Gly Glu Ser Gly Ser Gly Ser Gln
            20                  25                  30

Cys Thr Tyr Val Asn Ser Ile Ser Ser Gly Val Ser Trp Ser Thr
            35                  40                  45

Thr Trp Asn Trp Ser Gly Gly Ser Thr Ser Val Lys Ser Tyr Ala Asn
50                  55                  60

Ser Gln Leu Ser Gly Leu Thr Lys Lys Leu Val Ser Asn Leu Gln Ser
65                  70                  75                  80

Ile Pro Thr Ser Val Gln Trp Ser Tyr Ser Asn Thr Asn Ile Val Ala
                85                  90                  95

Asp Val Ser Tyr Asp Leu Phe Thr Ala Ala Asp Ile Asn His Val Thr
            100                 105                 110

Tyr Ser Gly Asp Tyr Glu Leu Met Ile Trp Leu Gly Lys Tyr Gly Gly
            115                 120                 125

Ala Gln Pro Leu Gly Ser Gln Ile Gly Thr Ala Asn Val Gly Gly Ala
            130                 135                 140

Thr Trp Gln Leu Trp Tyr Gly Val Asn Gly Ser Gln Lys Thr Tyr Ser
145                 150                 155                 160

Phe Val Ala Ser Ser Gln Thr Thr Ser Trp Asn Gly Asp Ile Leu Gln
                165                 170                 175

Phe Phe Lys Tyr Leu Gln Ser Asn Gln Gly Phe Pro Ala Ser Ser Gln
            180                 185                 190

Tyr Leu Ile Asp Leu Gln Phe Gly Thr Glu Pro Phe Thr Gly Ser Gln

```
                      195                 200                 205
Thr Thr Leu Thr Val Asn His Trp Ser Ala Ser Val Asn
    210                 215                 220
```